United States Patent
Huang et al.

(10) Patent No.: US 9,955,944 B2
(45) Date of Patent: *May 1, 2018

(54) TIME REVERSAL AND PHASE COHERENT MUSIC TECHNIQUES FOR SUPER-RESOLUTION ULTRASOUND IMAGING

(71) Applicant: LOS ALAMOS NATIONAL SECURITY, LLC, Los Alamos, NM (US)

(72) Inventors: Lianjie Huang, Los Alamos, NM (US); Yassin Labyed, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 875 days.

This patent is subject to a terminal disclaimer.

(21) Appl. No.: 14/339,791

(22) Filed: Jul. 24, 2014

(65) Prior Publication Data

US 2014/0364733 A1    Dec. 11, 2014

Related U.S. Application Data

(63) Continuation of application No. PCT/US2013/024550, filed on Feb. 3, 2013.

(Continued)

(51) Int. Cl.
*A61B 8/00* (2006.01)
*A61B 8/08* (2006.01)
(Continued)

(52) U.S. Cl.
CPC .............. *A61B 8/0825* (2013.01); *A61B 8/13* (2013.01); *A61B 8/5207* (2013.01);
(Continued)

(58) Field of Classification Search
None
See application file for complete search history.

(56) References Cited

U.S. PATENT DOCUMENTS

| 4,075,883 A | 2/1978 | Glover |
| 4,582,065 A | 4/1986 | Adams |
| (Continued) | | |

FOREIGN PATENT DOCUMENTS

| JP | 2009189867 A | 8/2009 |
| KR | 1020100075011 A | 7/2010 |
| (Continued) | | |

OTHER PUBLICATIONS

Devaney et al. Super-resolution Processing of Multi-static Data Using Time Reversal and MUSIC. 2000. [Online]: http://www.ece.neu.edu/faculty/devaney/ajd/preprints.htm. (pp. 4, 10).*

(Continued)

*Primary Examiner* — Jonathan Cwern
(74) *Attorney, Agent, or Firm* — Lewis Roca Rothgerber Christie LLP

(57) ABSTRACT

Systems and methods for super-resolution ultrasound imaging using a windowed and generalized TR-MUSIC algorithm that divides the imaging region into overlapping sub-regions and applies the TR-MUSIC algorithm to the windowed backscattered ultrasound signals corresponding to each sub-region. The algorithm is also structured to account for the ultrasound attenuation in the medium and the finite-size effects of ultrasound transducer elements. A modified TR-MUSIC imaging algorithm is used to account for ultrasound scattering from both density and compressibility contrasts. The phase response of ultrasound transducer elements is accounted for in a PC-MUSIC system.

14 Claims, 20 Drawing Sheets

Related U.S. Application Data

(60) Provisional application No. 61/594,966, filed on Feb. 3, 2012.

(51) Int. Cl.
   *A61B 8/13* (2006.01)
   *G01S 7/52* (2006.01)
   *G01S 15/89* (2006.01)

(52) U.S. Cl.
   CPC ...... *G01S 7/52046* (2013.01); *G01S 15/8977* (2013.01); *A61B 8/5253* (2013.01); *G01S 7/52095* (2013.01); *G01S 15/8915* (2013.01); *G01S 15/8997* (2013.01)

(56) References Cited

U.S. PATENT DOCUMENTS

| | | | |
|---|---|---|---|
| 5,465,722 A * | 11/1995 | Fort | G01H 5/00 600/437 |
| 5,908,390 A | 6/1999 | Matsushima | |
| 6,186,951 B1 | 2/2001 | Lizzi | |
| 2001/0020130 A1 | 9/2001 | Gee | |
| 2002/0099290 A1 | 7/2002 | Haddad | |
| 2002/0173722 A1 | 11/2002 | Hoctor | |
| 2003/0158481 A1 | 8/2003 | Stotzka | |
| 2004/0034307 A1 | 2/2004 | Johnson et al. | |
| 2006/0058678 A1 | 3/2006 | Vitek | |
| 2006/0173304 A1 | 8/2006 | Wang | |
| 2006/0184020 A1 | 8/2006 | Sumi | |
| 2006/0293597 A1 | 12/2006 | Johnson et al. | |
| 2007/0100239 A1 | 5/2007 | Nair | |
| 2008/0045864 A1 | 2/2008 | Candy | |
| 2008/0081993 A1 | 4/2008 | Waki | |
| 2008/0229832 A1 | 9/2008 | Huang | |
| 2008/0294043 A1 | 11/2008 | Johnson et al. | |
| 2008/0319318 A1 | 12/2008 | Johnson et al. | |
| 2009/0076389 A1 | 3/2009 | Jin | |
| 2009/0099456 A1 | 4/2009 | Burcher | |
| 2010/0157732 A1 | 6/2010 | Saenger | |
| 2011/0118984 A1 | 5/2011 | Chevion | |
| 2011/0125014 A1 | 5/2011 | Derode | |
| 2011/0131020 A1 | 6/2011 | Meng | |

FOREIGN PATENT DOCUMENTS

| | | |
|---|---|---|
| WO | WO2007133882 A2 | 11/2007 |
| WO | WO2011103303 A2 | 8/2011 |

OTHER PUBLICATIONS

Nguyen et al. The DORT solution in acoustic inverse scattering problem of a small elastic scatterer. 2010. Ultrasonics, vol. 50 Issue 8, pp. 831, 832.*

Devaney et al. Time-reversal-based imaging and inverse scattering of multiply scattering point targets. 2005. The Journal of the Acoustical Society of America, vol. 118 No. 5, pp. 3132.*

Szabo et al. 2004. Determining the pulse-echo electromechanical characteristic of a transducer using flat plates and point targets. The Journal of the Acoustical Society of America, vol. 116 No. 1, p. 91.*

Cobbold. (2007). Foundations of Biomedical Ultrasound. New York: Oxford University Press. (pp. 110-111).*

Yao et al. A Fast Algorithm to Calculate Ultrasound Pressure Fields From Single-Element Transducers. 1989. IEEE Transactions on Ultrasonics, Ferroelectrics and Frequency Control, vol. 36 No. 4, p. 446.*

Lemoult et al. Time Reversal in Subwavelength-Scaled Resonant Media: Beating the Diffraction Limit. 2011. International Journal of Microwave Science and Technology, vol. 2011, Article ID 425710, p. 4.*

Ikedo et al. Development of a fully automatic scheme for detection of masses in whole breast ultrasound images. 2007. Medical Physics, vol. 34 No. 11, pp. 4381.*

Labyed et al. Ultrasound Time-Reversal MUSIC Imaging With Diffraction and Attenuation Compensation. 2012. IEEE Transactions on Ultrasonics, Ferroelectrics, and Frequency Control, vol. 59 No. 10, p. 2188.*

Korean Intellectual Property Office (KIPO), International Search Report and Written Opinion dated May 30, 2013, Counterpart PCT International Application No. PCT/US2013/024550, pp. 1-11, with claims searched, pp. 12-21.

Korean Intellectual Property Office (KIPO), International Search Report and Written Opinion dated May 30, 2013, PCT International Application No. PCT/US2013/024512, pp. 1-10, with claims searched, pp. 11-21.

Office action dated May 2, 2017 issued in co-pending U.S. Appl. No. 14/339,728.

Office action dated Mar. 31, 2017 issued in co-pending U.S. Appl. No. 14/339,712.

Office action dated Apr. 4, 2017 issued in co-pending U.S. Appl. No. 14/339,738.

Office action dated May 9, 2017 issued in co-pending U.S. Appl. No. 14/339,780.

Office action dated May 1, 2017 issued in co-pending U.S. Appl. No. 14/339,759.

Office action dated Apr. 19, 2017 issued in co-pending U.S. Appl. No. 14/339,770.

Anagaw et al., "Full Waveform Inversion with Total Variation Regularization," Recovery—2011 CSPG CSEG CWLS Convention, pp. 1-4.

Boonyasiriwat et al., 3D Multisource Full-Waveform Inversion using Dynamic Random Phase Encoding,: Society of Exploration Geophysics Technical Program Expanded Abstracts, 2010, pp. 1044-1049.

Cuiping, Li et al., "In Vivo Breast Sound-Speed Imaging with Ultrasound Tomography," Ultrasound in Medicine and Biology, Oct. 2009, vol. 35, No. 10, pp. 1616-1628.

Duric et al. "Development of Ultrasound Tomography for Breast Imaging: Technical Assessment," Medical Physics 32(5):1375-86.

Fichtner et al. "Full Seismic Waveform Tomography for upper-mantle structure in the Australasian region using Adjoint Methods," Geophys. J. Int. (2009) 179, pp. 1703-1725.

Huang et al., "A Rapid and Robust Numerical Algorithm for Sensitivity Encoding with Sparsity Constraints: Self-Feeding Sparse SENSE," Magnetic Resonance in Medicine, 2010, 64:1078-1088.

Margrave et al., Full Waveform Inversion with Wave Equation Migration and Well Control, CREWES Research Report vol. 22, 2010, pp. 1-20.

Sallard et al . . . "Use of a priori Information for the Deconvolution of Ultrasonic Signals," Rev. of Prog. in Quantitative Nondestructive Evaluation, vol. 17, Plenum Press, New York, 1998, pp. 735-742.

Sumi, C., "Spatially variant regularization for the Deconvolution of Ultrasonic Signals," Rev. of Prog. in Quantitative Nondestructive Evaluation, J Med Ultrasonics (2007) 34:125-131, Mar. 8, 2007.

Tai, et al. "Image Denoising Using TV-Stokes Equation with an Orientation-Matching Minimization" Space and Variational Methods in Computer Vision, Lecture Notes in Computer Science, vol. 5567, 2009, pp. 1-12.

Tape et al., "Finite-Frequency Tomography Using Adjoint Methods-Methodology and Examples Using Membrane Surface Waves," Geophys. J. Int. (2007) 168, pp. 1105-1129.

Waag et al., A Ring Transducer System for Medical Ultrasound Research, 2006, IEEE Transactions on Ultrasonics, Ferroelectrics, and Frequency control, vol. 53, No. 10, p. 1709.

Korean Intellectual Property Office (KIPO) International Search Report and Written Opinion dated Jun. 2, 2013, PCT International Application No. PCT/US2013/024676, pp. 1-10, with claims searched, pp. 11-18.

Korean Intellectual Property Office (KIPO) International Search Report and Written Opinion dated May 30, 2013, PCT International Application No. PCT/US2013/024545, pp. 1-12, with claims searched, pp. 13-20.

(56) References Cited

OTHER PUBLICATIONS

Korean Intellectual Property Office (KIPO) International Search Report and Written Opinion dated May 30, 2013, COUNTERPART PCT International Application No. PCT/US2013/024656, pp. 1-10, with claims searched, pp. 11-16.
Korean Intellectual Property Office (KIPO) International Search Report and Written Opinion dated May 30, 2013, PCT International Application No. PCT/US2013/024662, pp. 1-10, with claims searched, pp. 11-19.
Korean Intellectual Property Office (KIPO) International Search Report and Written Opinion dated May 30, 2013, PCT International Application No. PCT/US2013/024539, pp. 1-16, with claims searched, pp. 17-24.

* cited by examiner

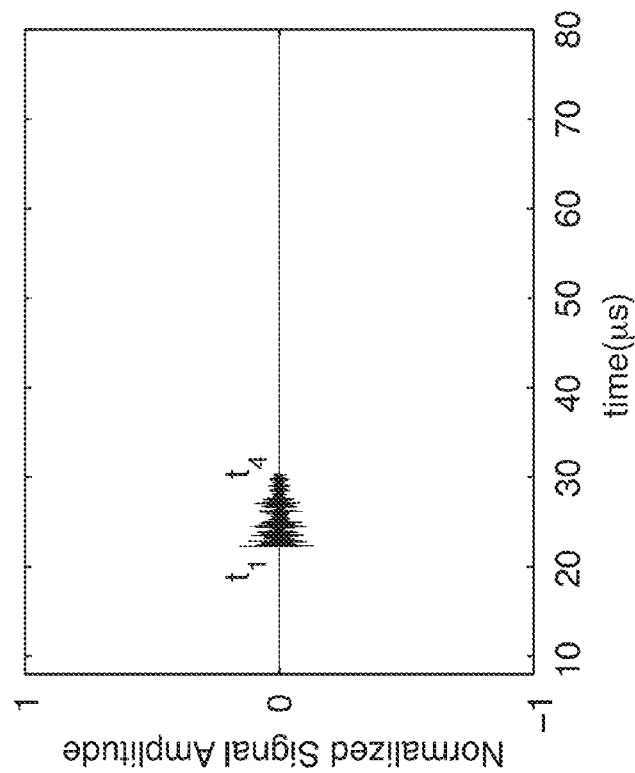
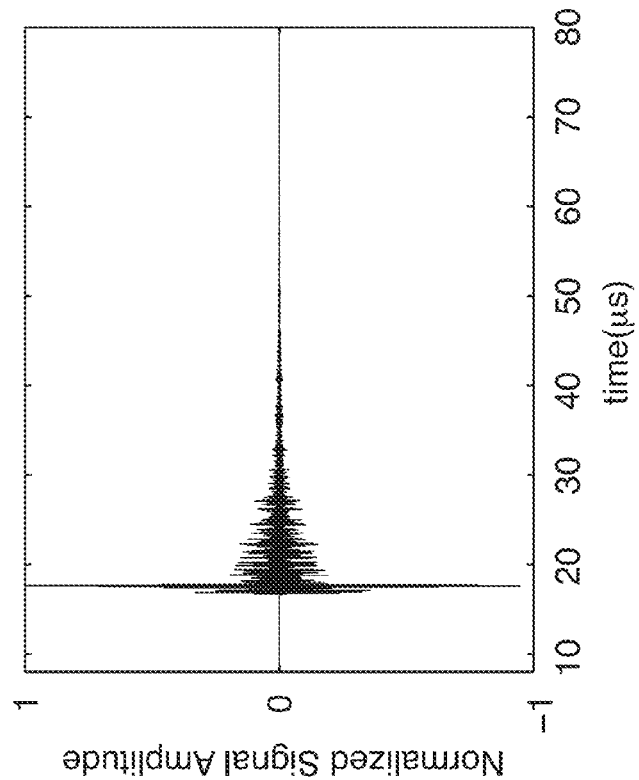

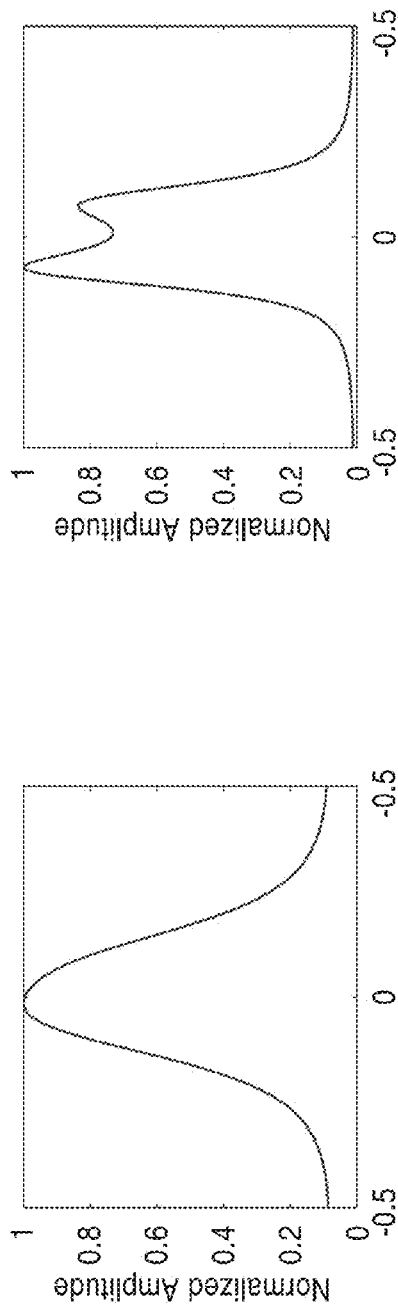
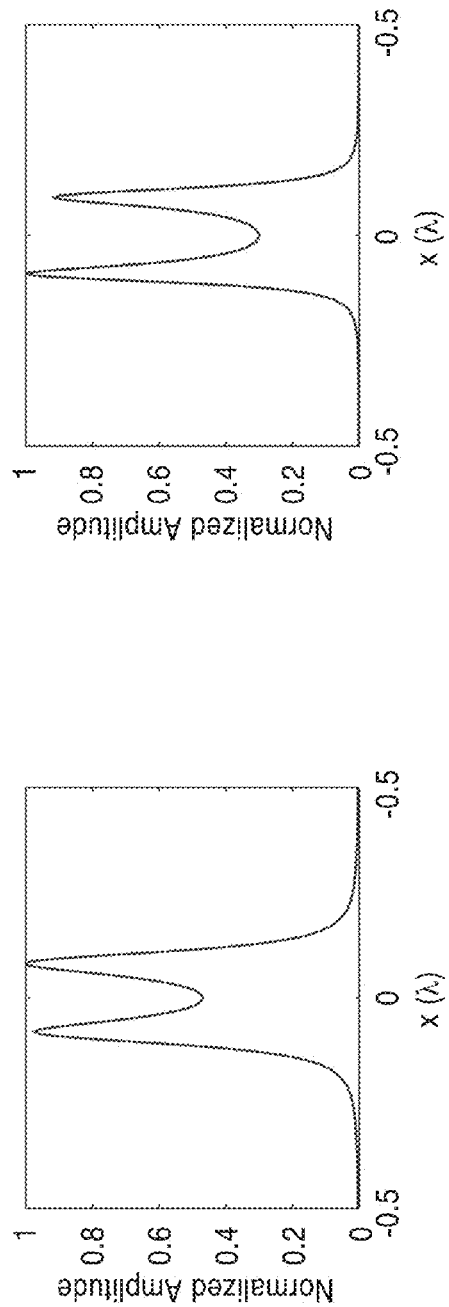
FIG. 10A  FIG. 10B  FIG. 10C  FIG. 10D

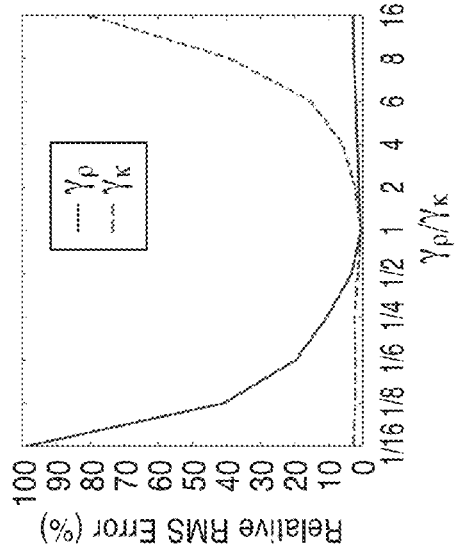
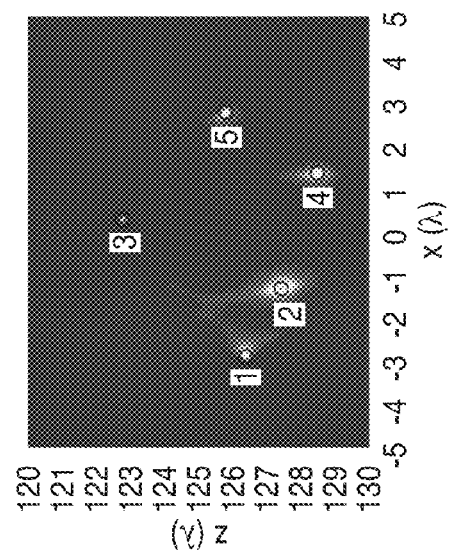
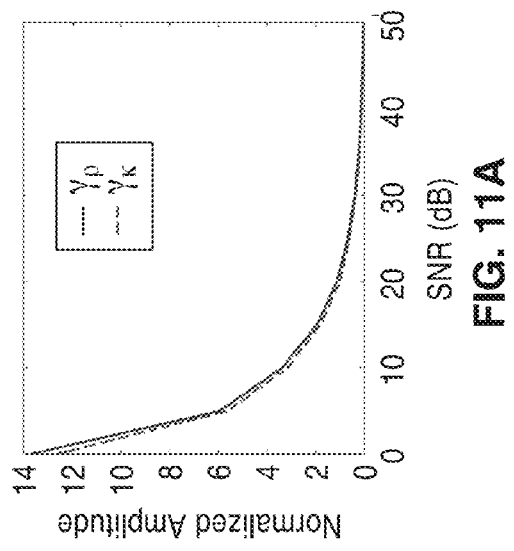
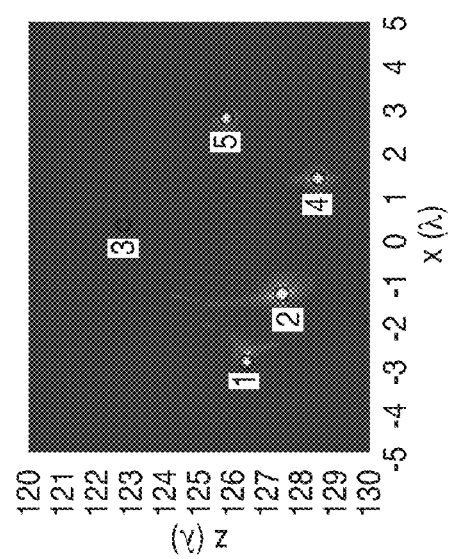
FIG. 11A
FIG. 11B
FIG. 12A
FIG. 12B

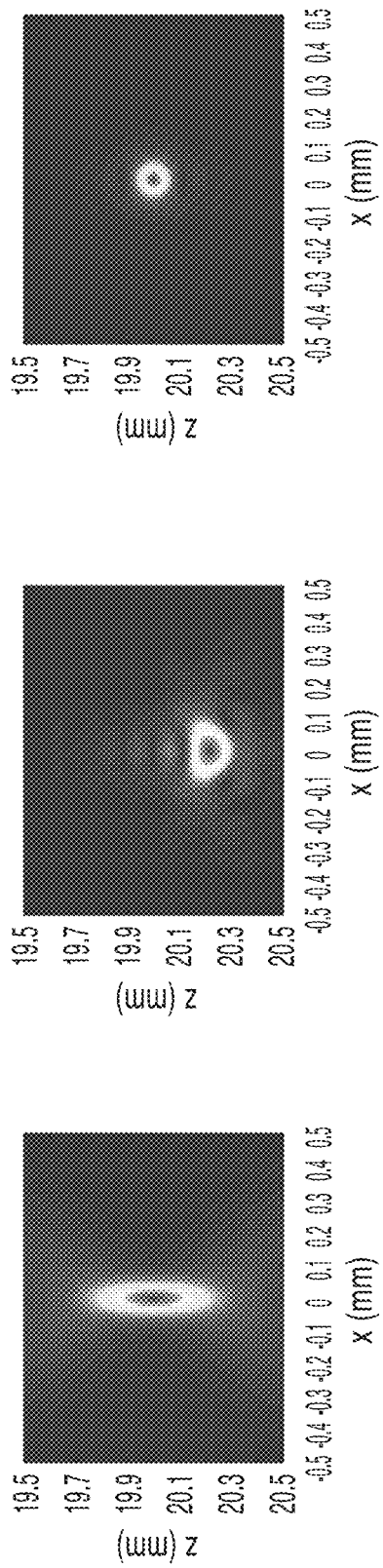

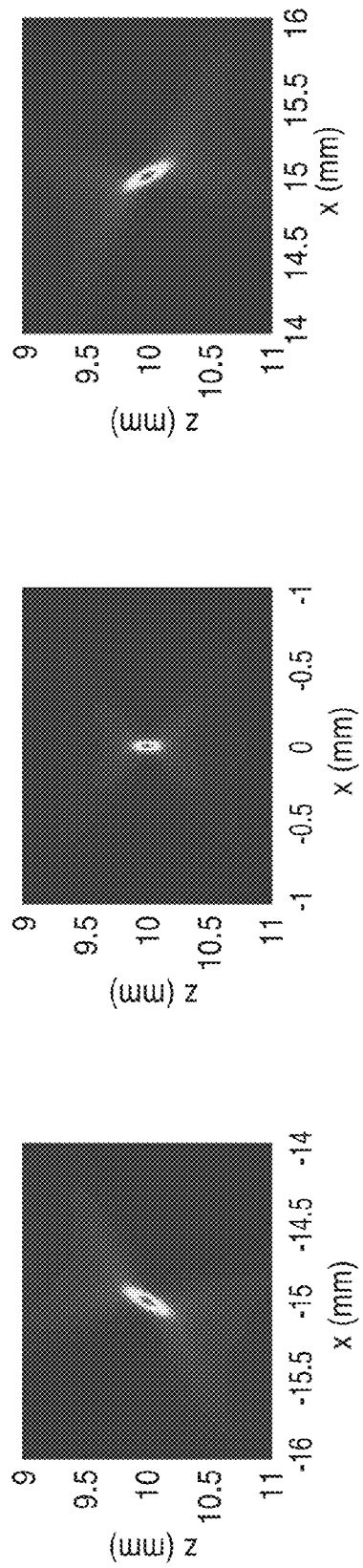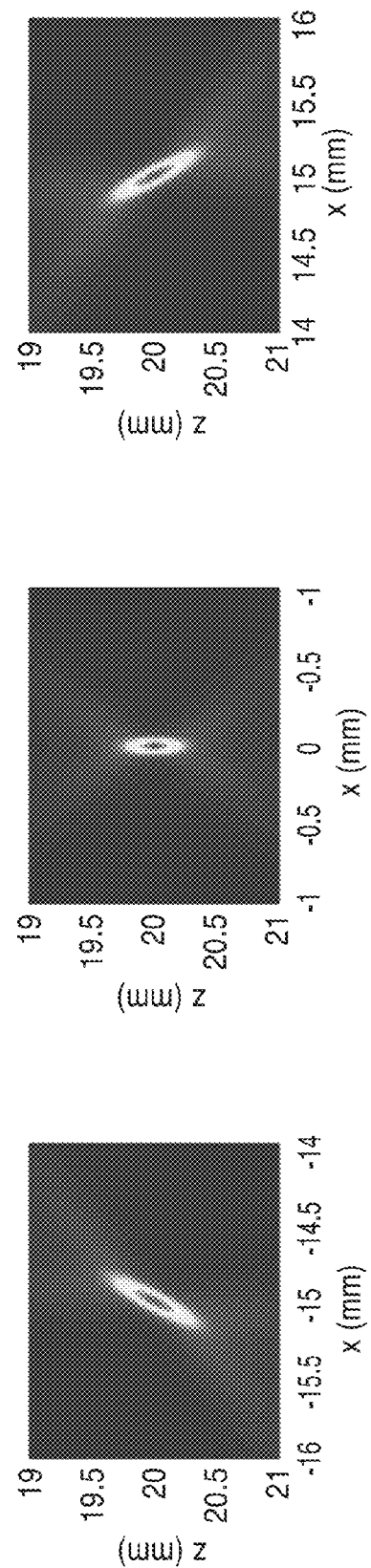
FIG. 17A, FIG. 17B, FIG. 17C, FIG. 17D, FIG. 17E, FIG. 17F

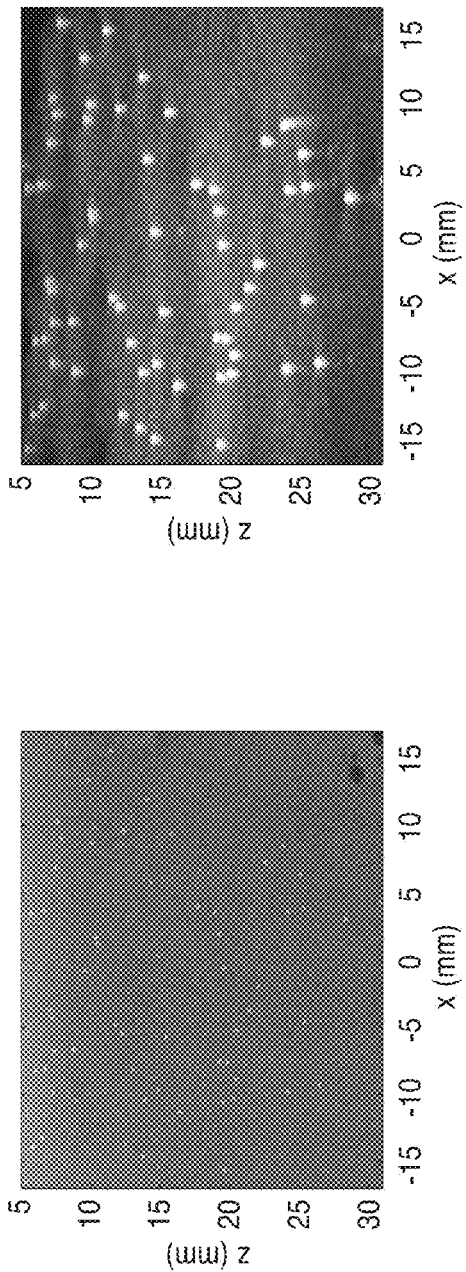
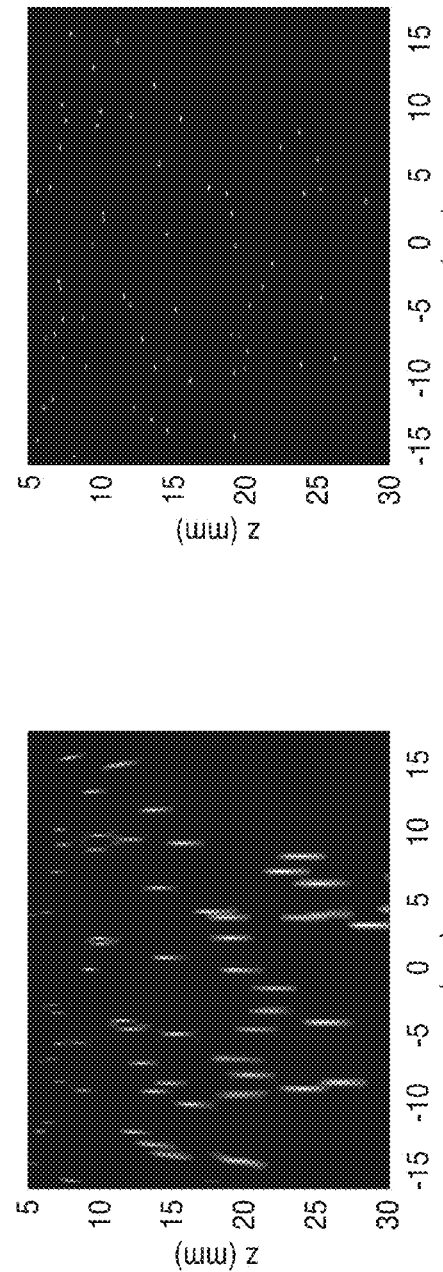
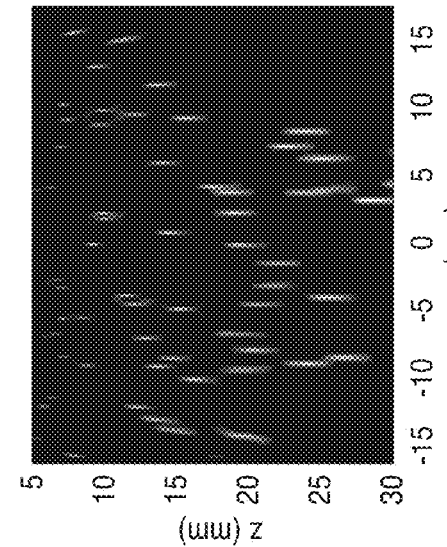

TIME REVERSAL AND PHASE COHERENT MUSIC TECHNIQUES FOR SUPER-RESOLUTION ULTRASOUND IMAGING

CROSS-REFERENCE TO RELATED APPLICATIONS

This application is a 35 U.S.C. § 111(a) continuation of PCT international application number PCT/US2013/024550 filed on Feb. 3, 2013, incorporated herein by reference in its entirety, which claims priority to, and the benefit of, U.S. provisional patent application Ser. No. 61/594,966 filed on Feb. 3, 2012, incorporated herein by reference in its entirety. Priority is claimed to each of the foregoing applications.

The above-referenced PCT international application was published as PCT International Publication No. WO 2013/116813 on Aug. 8, 2013, incorporated herein by reference in its entirety.

STATEMENT REGARDING FEDERALLY SPONSORED RESEARCH OR DEVELOPMENT

This invention was made with Government support under Contract No. DE-AC52-06NA25396 awarded by the Department of Energy. The Government has certain rights in the invention.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to imaging and more particularly to ultrasound imaging.

2. Description of Related Art

Time-reversal (TR) methods have received considerable interest in many areas, with applications ranging from the destruction of kidney stones, to the detection of flaws in solids, and to ultrasound medical imaging. One of these methods is the Time-Reversal with Multiple Signal Classification (TR-MUSIC) imaging algorithm developed by Devaney. This algorithm combines TR focusing with the MUSIC signal-subspace algorithm.

Numerical and experimental studies that used the MUSIC algorithm with TR imaging showed that when the targets are much smaller than the ultrasound wavelength, images with sub-wavelength resolution can be achieved. The high-resolution capability of TR-MUSIC imaging may find many applications in medical ultrasound. One area of interest is the detection of breast micro-calcifications, which are the first sign of breast cancer for more than half of all breast cancer cases.

The TR-MUSIC algorithm assumes that the ultrasound attenuation of the medium is negligible, and does not account for the finite-size effects of the transducer elements. In addition, the algorithm is applicable only when the number of point scatterers is fewer than the number of elements in a transducer array.

Recently, a new method has been developed named phase-coherent MUSIC (PC-MUSIC), which details an algorithm that modifies the standard TR-MUSIC to make use of phase information. However, this method ignores the phase response of transducer elements, and thus has little efficacy over standard TR-MUSIC.

Accordingly, an object of the present invention is a generalized TR-Music method to account for ultrasound tissue attenuation and the finite-size effects of transducer elements. Another object is a windowed TR-MUSIC method for imaging point scatterers when their number exceeds the number of ultrasound transducers in the scanner array, or imaging extended targets. At lease some of these objectives will be met in the description below.

BRIEF SUMMARY OF THE INVENTION

Time-reversal imaging with Multiple Signal Classification (TR-MUSIC) is an algorithm for detecting small targets embedded in a medium. This algorithm can produce images with sub-wavelength resolution when the targets are point-like, and when the number of scatterers is fewer than the number of ultrasound transducer elements used to interrogate the medium.

The system and methods of the present invention are directed to a new algorithm based on TR-MUSIC for imaging point scatterers when their number exceeds the number of ultrasound transducer elements used to interrogate the medium, or when the medium contains numerous extended targets that cannot be considered as point scatterers.

In a preferred embodiment, the systems methods of the present invention divide the imaging region into overlapping sub-regions and apply the TR-MUSIC algorithm to the windowed backscattered ultrasound signals corresponding to each sub-region. The images of all sub-regions are then combined to form the total image by interpolation of the images from the overlapped sub-regions.

Imaging results of numerical and phantom data show that when the number of scatterers within each sub-region is much smaller than the number of ultrasound transducer elements, the methods of the present invention yield super-resolution images with accurate scatterer localization.

The generalized TR-MUSIC algorithm of the present invention is also structured to account for the ultrasound attenuation in the medium and the finite-size effects of the ultrasound transducer elements. The generalized TR-MUSIC algorithm yields higher-resolution ultrasound images compared to those obtained without accounting for the ultrasound attenuation or the finite-size effects of ultrasound transducer elements.

The axial and lateral resolutions of the algorithm of the present invention were evaluated with respect to the effect of noise on the resolution of the images. Computer simulations and tissue-mimicking phantom data were acquired with a real-time synthetic-aperture ultrasound system to demonstrate the improved capability of the windowed TR-MUSIC algorithm. The windowed time-reversal MUSIC technique has the potential to detect breast microcalcifications.

In accordance with a preferred method of the present invention, the TR-MUSIC algorithm is generalized to account for the ultrasound attenuation in the interrogated medium, and the finite-size effects of the transducer elements.

In a preferred embodiment, a windowed TR-MUSIC algorithm is also used to image point scatterers, with high resolution even when their number exceeds the number of transducer elements.

Compared with the original MUSIC method, the generalized TR-MUSIC method of the present invention includes the following new features:

1) Accounts for the ultrasound attenuation in the tissue. This is accomplished by introducing the complex wavenumber in Eq. 4. The complex wavenumber contains the amplitude attenuation coefficient.

2) Accounts for the finite-size effects of ultrasound transducer elements. This is achieved by the integration in Eq. 16. In contrast, the original MUSIC method uses a point source Green's function.

3) Accounts for the electro-mechanical responses (time response) and their variations in the element-to-element sensitivity.

The generalized TR-MUSIC technique of the present invention takes the above three aspects into account.

In one embodiment of the present invention, the windowing method is incorporated into the generalized TR-MUSIC method. The original TR-MUSIC technique is valid only when the number of small (point) scatterers is fewer than the number of ultrasound transducer elements. The windowed TR-MUSIC method of the present invention can produce super-resolution images even when the number of small (point) scatterers exceeds the number of ultrasound transducer elements, and when the imaging plane contains numerous extended targets.

The windowed TR-MUSIC method of the present invention uses ultrasound data acquired using a synthetic-aperture ultrasound system. The investigational synthetic-aperture ultrasound system of the present invention allows acquisition of patient ultrasound data in real time. In the system, each element of the transducer array transmits ultrasound sequentially, and all elements in the transducer array simultaneously record ultrasound signals scattered from the tissue after each element is fired. The features of the system and method of the present invention provide a real-time synthetic-aperture system that can be used for patient data acquisition.

In a synthetic-aperture ultrasound system, ultrasound from each element of a transducer array or a virtual source of multiple elements propagates to the entire imaging domain, and all elements in the transducer array receive ultrasound signals reflected/scattered from the imaging region. Therefore, synthetic-aperture ultrasound data contain information of ultrasound reflected/scattered from all possible directions from the imaging domain to the transducer array. In contrast, the conventional ultrasound system records only 180° backscattered signals.

In a further aspect, a modified TR-MUSIC imaging algorithm is used to account for ultrasound scattering from both density and compressibility contrasts. In this modified TR-MUSIC imaging algorithm, an inter-element response matrix K for point scatters with density contrasts as well as compressibility contrasts is generated. Singular-value decomposition of the matrix K and the MUSIC algorithm are used to form a pseudo-spectrum that peaks at the locations of the point scatterers that may have the density contrast and/or the compressibility contrast relative to the background medium. The matrix K and information about the locations of the point scatterers is used to develop a linear-least-squares method to estimate the density and compressibility contrasts of the point scatterers.

In another aspect of the present invention, the phase response of ultrasound transducer elements is accounted for in a PC-MUSIC system and methods to achieve super resolution and accurate target localization. Because the phase response of transducer elements may not be known beforehand, another aspect is an experimental method to estimate the phase response using measured signals scattered from a glass micro-sphere embedded in a tissue-mimicking phantom with a homogeneous background medium and a known sound speed.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 7E is a plot of a received time signal.

FIG. 7F is a plot of the resulting time signal after muting the time samples outside the time window that starts at time $t_1$ and ends at time $t_4$.

FIGS. 9B, 9D, and 9F show the profiles when the pseudo-spectra are calculated using the TR-MUSIC algorithm of FIG. 8.

Figure 8:
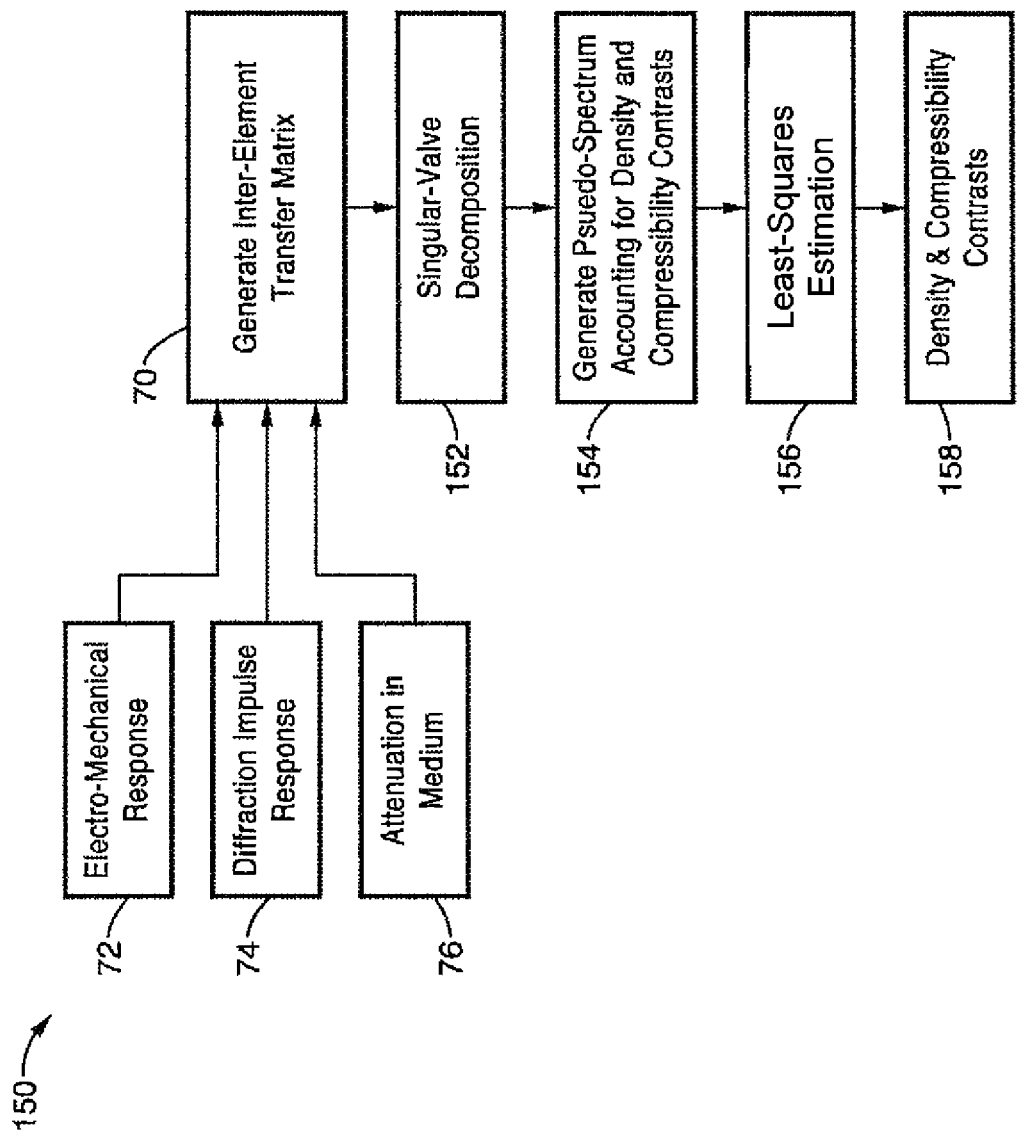
FIG. 8 is a flow diagram of the TR-MUSIC method using density and compressibility contrasts in accordance with the present invention.

FIG. 10A through FIG. 10D are plots of pseudo-spectra calculated using the TR-MUSIC algorithm of FIG. 8 when the SNR is 5 dB (FIG. 10A), 15 dB (FIG. 10B), 25 dB (FIG. 10C), and 35 dB (FIG. 10D). Zero-mean Gaussian noise is added to the inter-element response matrix. Lateral profiles at Z=25 mm of the normalized pseudo-spectra of two point targets separated laterally by $\lambda/2$. Both point target have $\gamma_\rho/\gamma_\kappa=1$.

FIG. 11A and FIG. 11B are plots of the relative root mean squared (RMS) error in the estimates of $\gamma_\kappa$ and $\gamma_\rho$ for a point target located at X=mm, Z=25 mm versus SNR when $\gamma_\rho/\gamma_\kappa=1$ (FIG. 11A) and versus $\gamma_\rho/\gamma_\kappa$ when SNR=25 dB (FIG. 11B).

FIG. 12A and FIG. 12B are images of five point targets randomly distributed in a 10λ×10λ centered at X=0 mm and Z=25 mm (125λ) obtained using (FIG. 12A) the original TR-MUSIC algorithm and (FIG. 12A) the modified TR-MUSIC algorithm of the present invention. The dynamic range of the images is 80 dB.

Figure 13:
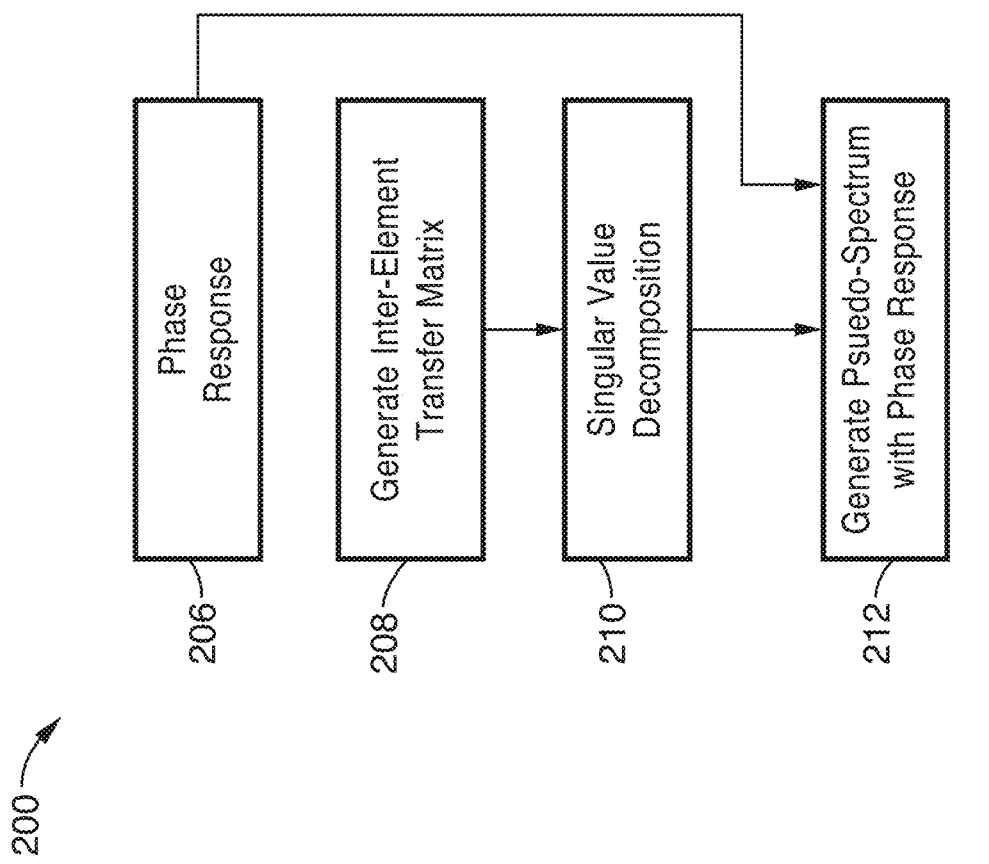

FIG. 13 is a flow diagram of a PC-MUSIC imaging method that compensates for phase response of transducers in accordance with the present invention.

Figure 14A:
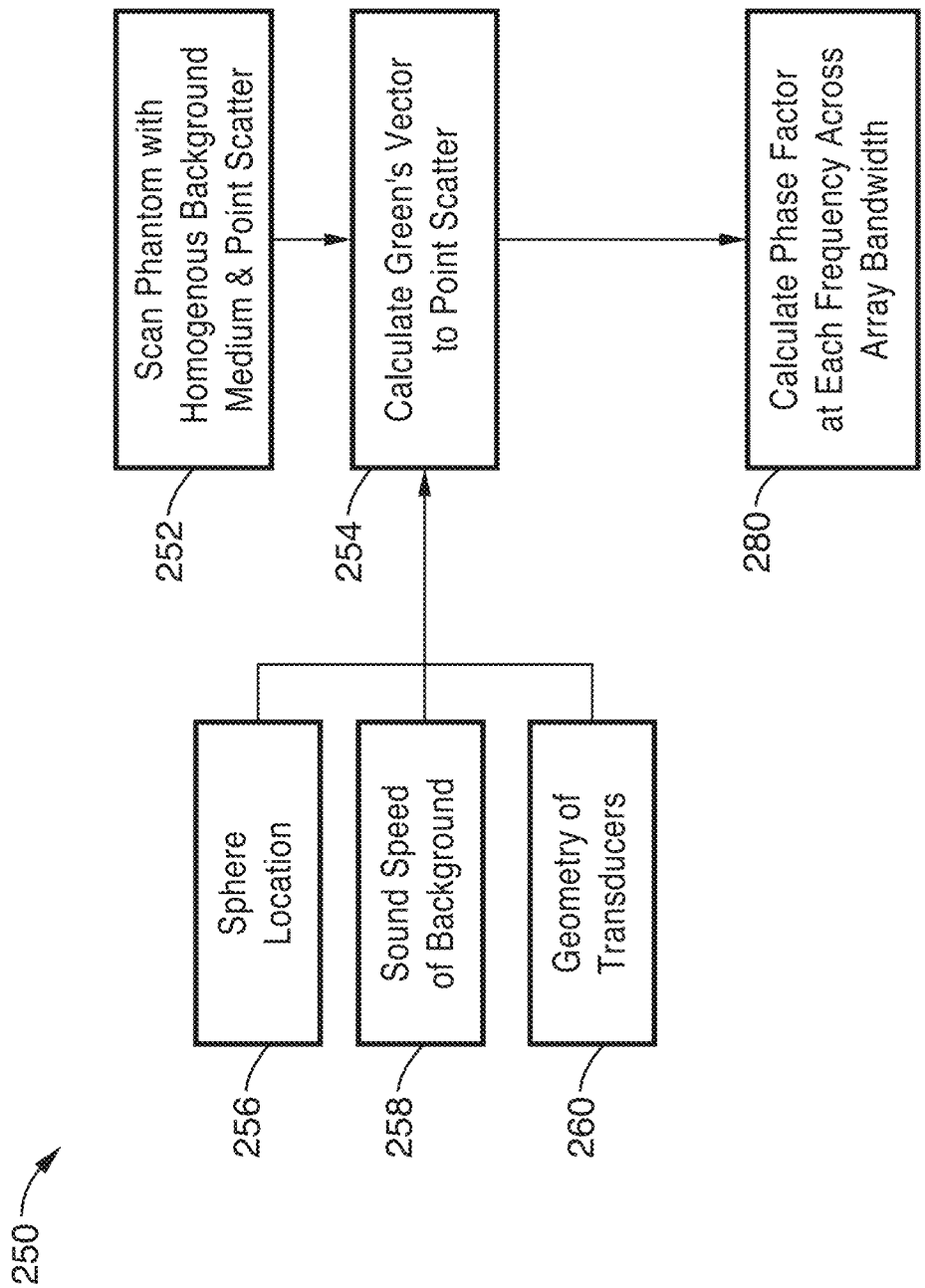

FIG. 14A is a flow diagram of an experimental method for obtaining the phase response of an array of transducers for use in the method of FIG. 13.

Figure 14B:
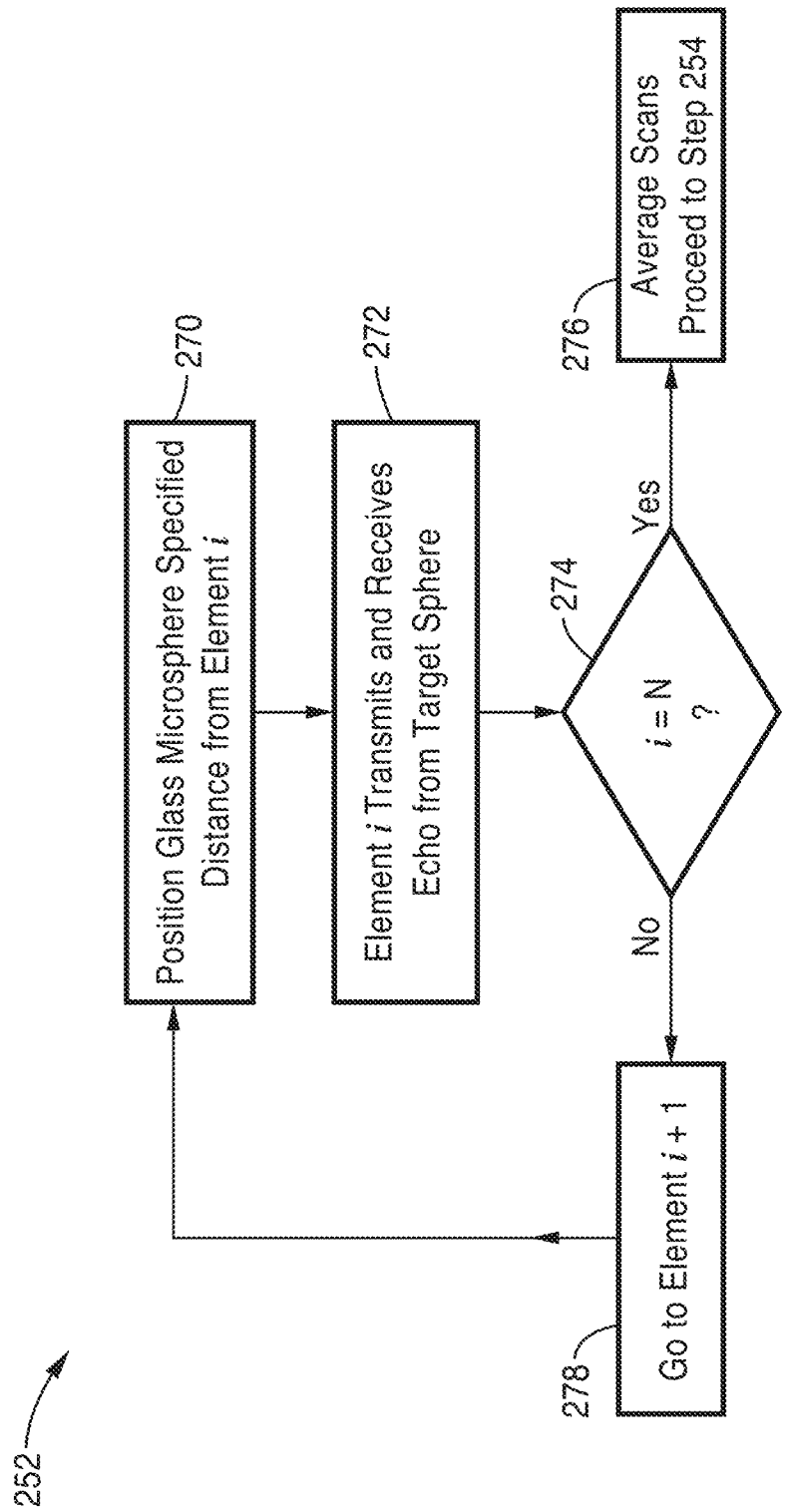

FIG. 14B is a flow diagram of a process for scanning a phantom for use in the experimental method of FIG. 14A.

FIG. 15A through FIG. 15C show images of the point scatterer located at (X, Z)=(0 mm, 20 mm)=(0λ, 100λ) obtained with TR-MUSIC (FIG. 15A), PC-MUSIC without phase-response compensation (FIG. 15B) and with phase-response compensation (FIG. 15C).

FIG. 16A through FIG. 16H show plots of the amplitudes (FIGS. 16A, 16C, 16E, 16G) and sine (FIGS. 16B, 16D, 16F, 16H) of the phases of the pseudo-spectra calculated at different points away (λ/4 for FIGS. 16C and 16D), (λ/2 for FIGS. 16E and 16F) and (λ for FIGS. 16G and 16H) below the scatterer location from the true location (X, Z)=(0 mm, 20 mm) (FIGS. 16A and 16B) of a single point scatterer. The solid and dashed and plots are obtained using TR-MUSIC and PC-MUSIC with phase response compensation, respectively. The vertical lines show the range of frequencies used to calculate the images of FIGS. 15A through 15C. The SNR is 10 Db.

FIG. 17A through FIG. 17F show images of a point scatterer obtained using the classical TR-MUSIC algorithm. The SNR is 10 dB. In each panel, the scatterer located at a different lateral (X) and axial (Z) position in the imaging plane ((X,Z)=(−75λ,50λ) for FIG. 17A), ((X,Z)=(0λ,50λ) for FIG. 17B), ((X,Z)=(75λ,50λ) for FIG. 17C), ((X,Z)=(−75λ,100λ) for FIG. 17D), ((X,Z)=(0λ,100λ) for FIG. 17E), ((X,Z)=(75λ,100λ) for FIG. 17F).

FIG. 18A through FIG. 18F show images of a point scatterer obtained using the PC-MUSIC algorithm with phase compensation. The SNR is 10 dB. In each panel, the scatterer located at a different lateral (X) and axial (Z) position in the imaging plane ((X,Z)=(−75λ,50λ) for FIG. 18A), ((X,Z)=(0λ,50λ) for FIG. 18B), ((X,Z)=(75λ,50λ) for FIG. 18C), ((X,Z)=(−75λ,100λ) for FIG. 18D), ((X,Z)=(0λ, 100λ) for FIG. 18E), ((X,Z)=(75λ,100λ) for FIG. 18F).

FIG. 19A through FIG. 19D show images of a phantom (Phantom 1) containing a homogeneous background and glass spheres with average diameters of 250 μm. The images are obtained using mammography (FIG. 19A), synthetic-aperture imaging (FIG. 19B), (c) TR-MUSIC (FIG. 19C), and the PC-MUSIC method with compensation of the phase response of the transducer elements (FIG. 19D) in accordance with the present invention.

DETAILED DESCRIPTION OF THE INVENTION

Figure 1:
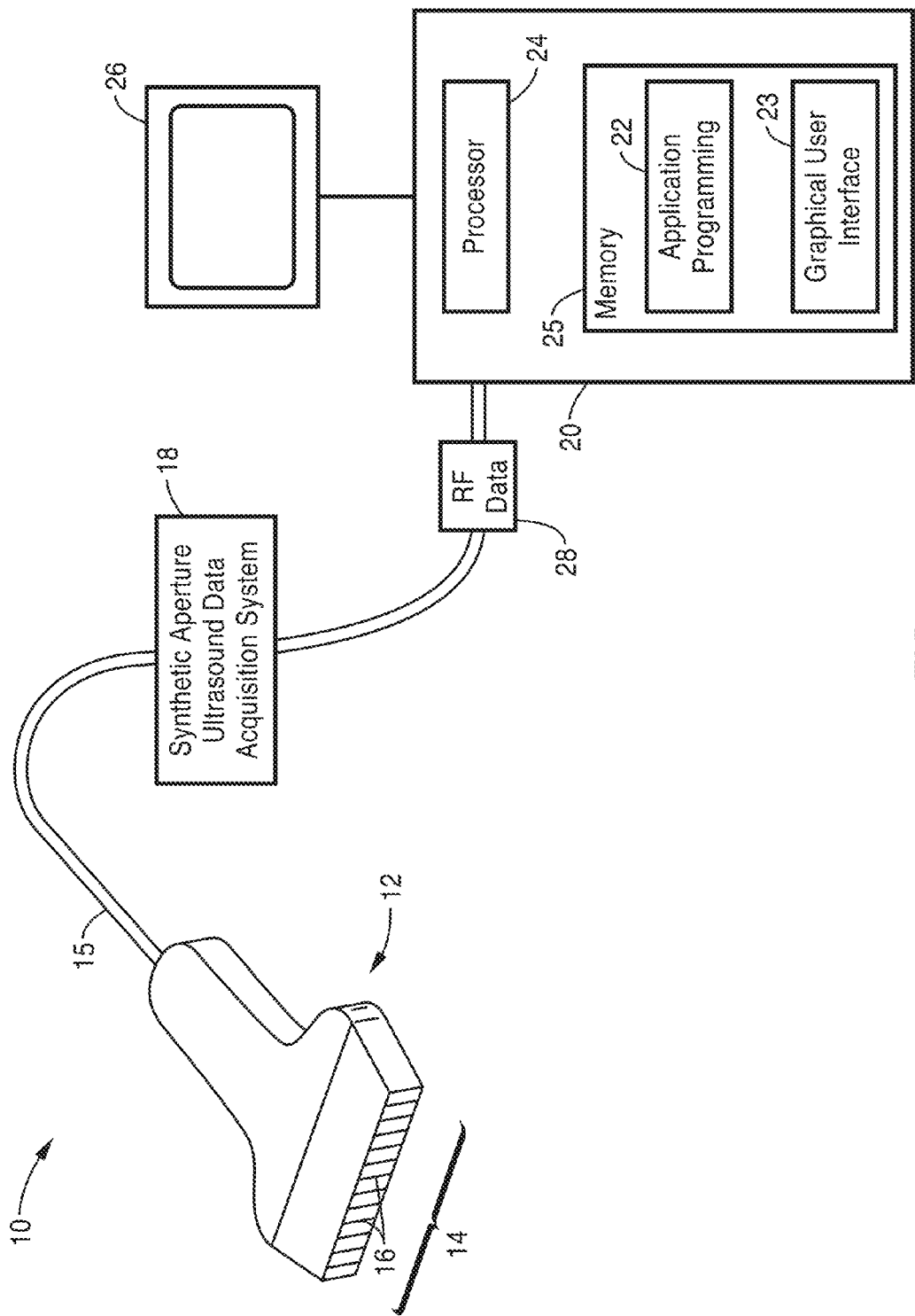
FIG. 1 is a schematic diagram of a synthetic-aperture ultrasound system in accordance with the present invention.

FIG. 1 is a schematic diagram of a synthetic-aperture ultrasound system 10 in accordance with the present invention. The system 10 includes a scanner 12 comprising a plurality of individual transducer elements 16 disposed within a linear array 14. The scanner 12 is coupled to a server or like computing apparatus 20 (e.g. with a cable 15 or other connection means such as, but not limited to, a wireless connections means) and synthetic aperture ultrasound data acquisition system 18 that outputs RF data 28 corresponding to readings acquired by the scanner 12.

Computer 20 comprises a processor 24 configured to operate one or more application programs 22 and graphical user interface 23 located within memory 25, wherein the application programs 22 may contain one or more algorithms or methods of the present invention for imaging a tissue medium for display on monitor 26, or other means. For example, the application programming 22 may comprise the programming configured for operating the sequential excitation method 50 shown in FIG. 3, the generalized TR-MUSIC method 66 shown in FIG. 4, the windowed TR-MUSIC method 100 shown in FIG. 5, the method 102 shown in FIG. 6 for dividing the image plane in accordance with the windowed method shown in FIG. 5, TR-MUSIC method 150 using density and compressibility contrasts shown in FIG. 8, the PC-MUSIC imaging method 200 that compensates for phase response of transducers shown in FIG. 13, the method 250 shown in FIG. 14A for obtaining the phase response of an array of transducers for use in the method of FIG. 13, and/or the process 252 shown in FIG. 14B for scanning a phantom for use in the of FIG. 14A.

Figure 2:
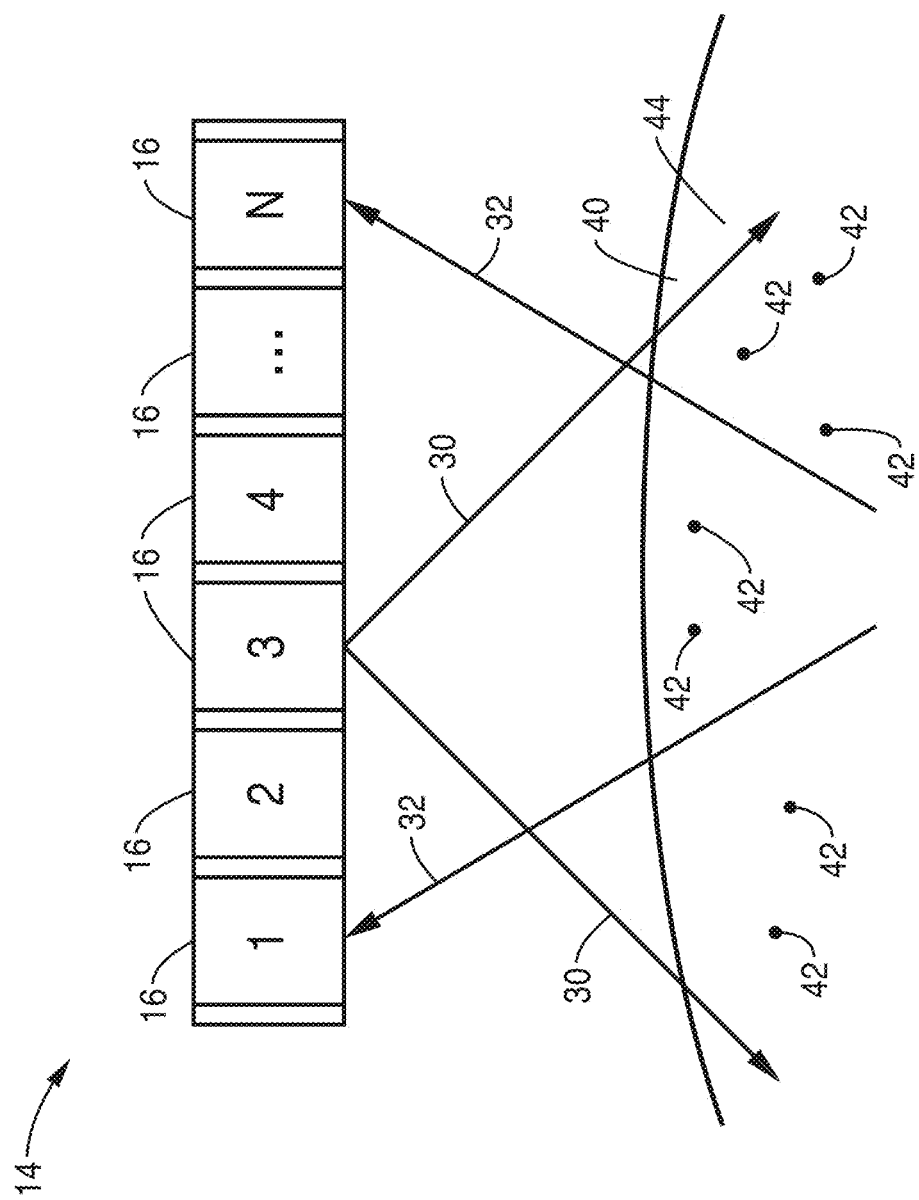
FIG. 2 is a schematic diagram of the scanner of the ultrasound system of FIG. 1 interrogating a region of tissue.

FIG. 2 is a schematic diagram of the array portion 14 of scanner 12 of the ultrasound system 10 shown in FIG. 1 illustrating interrogation of a region of tissue 44. In ultrasound imaging applications, TR focusing uses an array 14 of N transducers 16 acting in the transmit-receive mode.

Each element of the array 14 is excited sequentially (e.g. transducer 3 is shown in excitation mode) to generate an ultrasound field or signal 30 through the tissue surface 40 and into tissue region 44. The backscattered signals 32 are measured in parallel by all N elements 16, yielding the inter-element response matrix K(ω) of the array at the angular frequency ω. The matrix K(ω) is then used to compute the TR matrix T(ω)=K*(ω)K(ω). When the interrogated medium contains M well-resolved point scatterers 42, such that M<N, the TR operator has M eigenvectors with nonzero eigenvalues, and these eigenvectors correspond one-to-one with the different point scatterers 42.

Focusing on a single scatterer 42 can be achieved experimentally by using all elements 16 of the array 14 to back-propagate the eigenvector associated with that scatterer 42. If the geometry of the array 14 and the Green's function of the medium 44 are known, backpropagation can be computed numerically to obtain images of the different scatterers 42. The use of MUSIC with the TR operator yields a pseudo-spectrum that peaks at the locations of the point scatterers 42. This algorithm produces high-resolution images of point scatterers, even when the scatterers 42 are not well resolved by the imaging system.

Focusing on a single scatterer 42 can be achieved experimentally by using all elements 16 of the array 14 to back-propagate the eigenvector associated with that scatterer 42. If the geometry of the array 14 and the Green's function of the medium 44 are known, backpropagation can be computed numerically to obtain images of the different scatterers 42. The use of MUSIC with the TR operator yields a pseudo-spectrum that peaks at the locations of the point scatterers 42. This algorithm produces high-resolution images of point scatterers, even when the scatterers 42 are not well resolved by the imaging system.

Figure 3:
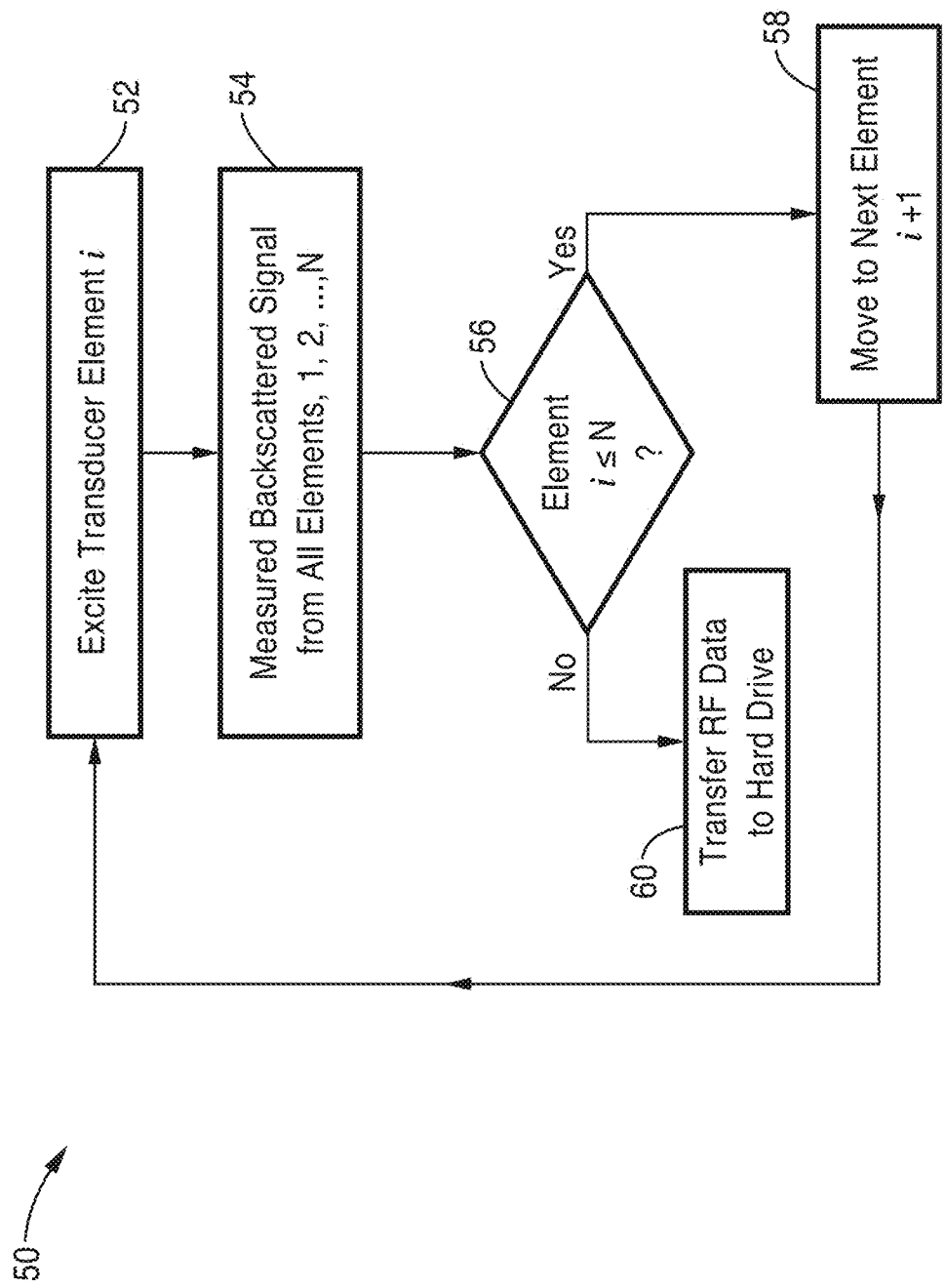
FIG. 3 is a flow diagram of a method for sequentially exciting a region of tissue in accordance with the present invention.

Still referring to FIG. 1 and FIG. 2, FIG. 3 shows flow diagram of a method 50 for sequentially exciting a region of tissue 44 in accordance with the present invention. At step 52, a first element (e.g. element 1 or i) of array 14 of N ultrasound transducer elements 16 is excited for interrogating an inhomogeneous medium 44. At step 54, the backscattered signals are measured by all elements 16 in the array 14. At step 56, the method evaluates whether all the elements 16 in the array 14 have been excited (and imaged). If the last element in the array 14 has not been reached, the method moves to the next element 16 in the array 14 at step 58, and repeats the process sequentially until the $N^{th}$ element is reached at step 60. At this point, the process 50 transfers the RF data to memory 25.

Generalized TR-MUSIC Algorithm

Figure 4:
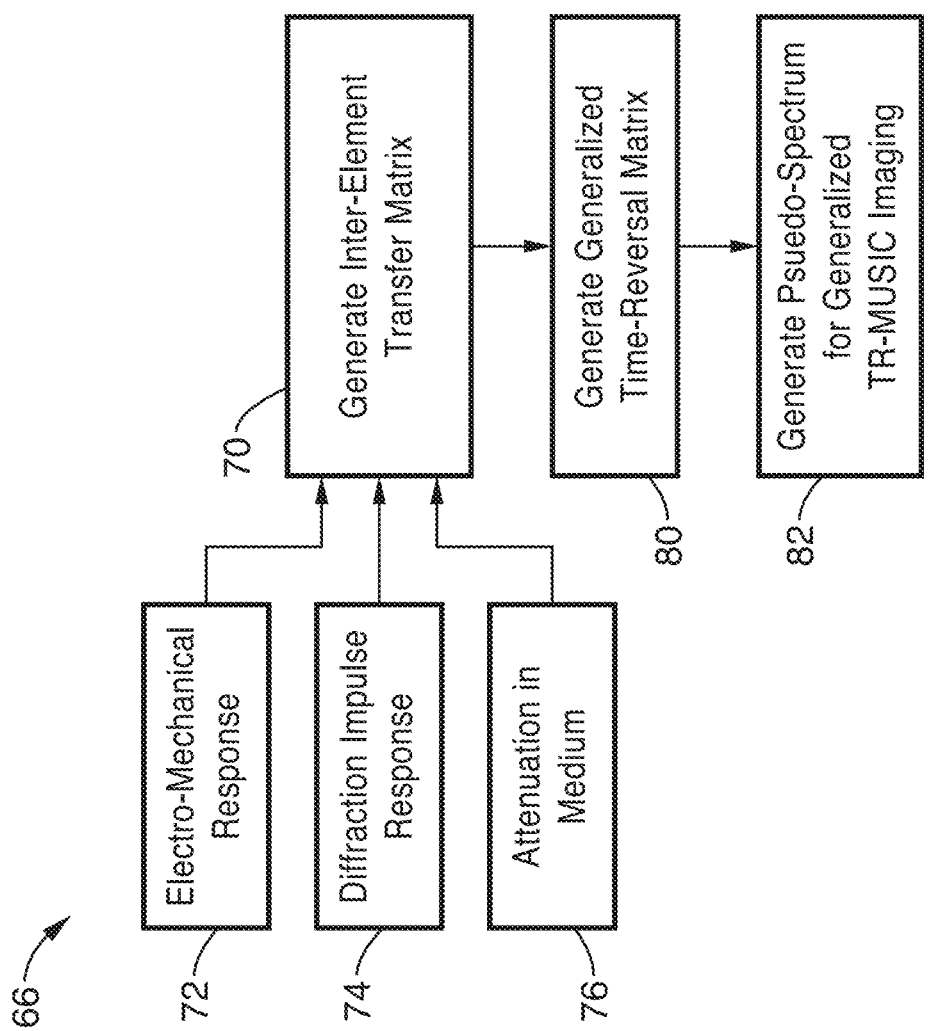
FIG. 4 is a flow diagram of the generalized TR-MUSIC method of the present invention.

FIG. 4 shows a flow diagram of the generalized TR-MUSIC method 66 of the present invention. In a preferred embodiment, the method 66 generates an inter-element transfer matrix at step 70, which incorporates the electro-mechanical response 72 of each element 16 in the array 14, the diffraction impulse response 74 of each element 16, and the attenuation 76 in the medium 44. Next, at step 80, the generalized time-reversal (TR) matrix is generated. Finally, a pseudo-spectrum for generalized TR-Music imaging is generated at step 82. Each of these steps will be described in further detail below.

The derivation of the expression for the matrix K is detailed as follows. First, the equation for the scattered field from an inhomogeneous medium is presented. Then, the transducer model is considered for calculation of the incident field. Finally, the wave-equation solution and the transducer model are combined to give the equation for the recorded electrical signal and form each element of the inter-element response matrix $K_{ij}(\omega)$.

The integral equation for the scattered pressure field from an inhomogeneous medium is given by Eq. 1:

$$p_s(r, \omega) = \int\int\int_{V_0} \{\underline{k}^2 \gamma_\kappa(r_0) p(r_0, \omega) g_0(\omega, r \mid r_0) - \nabla \cdot [\gamma_\rho(r_0) \nabla p(r_0, \omega)] g_0(r \mid r_0, \omega)\} dv_0 \quad \text{Eq. 1}$$

where $\omega$ is the angular frequency and $V_0$ is the scattering volume.

The fluctuation functions $\gamma_\kappa$ and $\gamma_\rho$ are measures of the relative compressibility and density differences between the scatterer and the surrounding medium given by:

$$\gamma_\kappa(r) = \frac{\kappa(r) - \kappa_0}{\kappa_0}, \quad \text{Eq. 2}$$

$$\gamma_\rho(r) = \frac{\rho(r) - \rho_0}{\rho(r)}, \quad \text{Eq. 3}$$

where $\rho_0$ is the average density, and $\kappa_0$ is the average compressibility of the medium.

The complex wave number $\underline{k}$ is $$\underline{k} = \frac{\omega}{c} - i\alpha, \quad \text{Eq. 4}$$

where $k=\omega/c$ is the real wave number, $\alpha$ is the amplitude attenuation coefficient, c is the average sound speed, and i is the imaginary unit. The free-space Green's function $g_0(\omega, r|r_0)$ is given by $$g_0(\omega, r \mid r_0) = \frac{\exp(-i\underline{k}|r - r_0|)}{4\pi|r - r_0|}. \quad \text{Eq. 5}$$

Because the wavenumber $\underline{k}$ of Eq. 4 is complex, the Green's function accounts for the attenuation in the medium shown in step 76 of FIG. 4.

In the following, the transducer model is used to derive the equation for the ultrasound incident field.

The ultrasound incident field is generated by an ultrasound transducer element 16, assuming no other sources exist in the medium 44. In the classical theory of sound in a fluid that exhibits viscous loss, the pressure phasor is given by $$p_{inc} = (r, \omega) = \frac{i\underline{k}^2 \Phi(r, \omega)}{\omega \kappa_0}, \quad \text{Eq. 6}$$

where $\Phi(r,\omega)$ is the velocity potential.

For a planar transmitting transducer element 16 of area S, the velocity potential is:

$$\Phi(r,\omega) = V_n(\omega) H(r,\omega), \quad \text{Eq. 7}$$

where $V_n(\omega)$ is the particle velocity normal to the surface of the transducer element, and $H(r,\omega)$ is the diffraction impulse response generated at step 74 of FIG. 4, and also may be referred to as the velocity-potential impulse response.

The particle velocity and the diffraction impulse response are given, respectively, by $$V_n(\omega) = W_t(\omega) E(\omega), \quad \text{Eq. 8}$$

and $$H(r, \omega) = \int\int_{S_t} \frac{\exp(-i\underline{k}|r - r_0|)}{2\pi|r - r_0|} ds_0, \quad \text{Eq. 9}$$

where the integral is evaluated over the surface of the transmitting element $S_t$, $W_t(\omega)$ is the transmitter electromechanical transfer function, and $E(\omega)$ is the input-voltage transfer function.

In Eq. 9, it is assumed that the acoustic velocity distribution is constant over the area $S_t$. Using the previous four equations, the incident pressure field is given by:

$$p_{inc}(r, \omega) = \frac{i\underline{k}^2}{\omega \kappa_0} W_t(\omega) E(\omega) \int\int_{S_t} \frac{\exp(-i\underline{k}|r - r_0|)}{2\pi|r - r_0|} ds_0. \quad \text{Eq. 10}$$

The spectrum of the electrical signal measured by the receiving transducer element is given by:

$$p_m(\omega) = W_r(\omega) \int\int_{S_r} p_s(r, \omega) ds, \quad \text{Eq. 11}$$

where the integral is evaluated over the receiving-element area $S_r$, and $W_r(\omega)$ is the receiver electro-mechanical transfer function. In Eq. 11, it is assumed that the spatial sensitivity of the scanner/detector 12 is constant across the area $S_r$.

Using this assumption, the sensitivity of the detector 12 is incorporated into $W_r(\omega)$. When the magnitudes of $\gamma_\rho$ and $\gamma_\kappa$ are small, the Born approximation is valid and the scattered wave from Eq. 1 becomes:

$$p_s(r, \omega) = \iiint_{V_0} \{k^2 \gamma_\kappa(r_0) p_{inc}(r_0, \omega) g_0(r \mid r_0, \omega) - \qquad \text{Eq. 12}$$

$$\nabla \cdot [\gamma_\rho(r_0) \nabla p_{inc}(r_0, \omega)] g_0(r \mid r_0) \} dv_0.$$

where the pressure field $p(r,\omega)$ is replaced by the incident field $p_{inc}(r,\omega)$ on the right-hand side of Eq. 1.

By substituting Eq. 12 and assuming that the scatterers are sufficiently far from the transducer element 16, such that $|r-r_0| \gg \lambda$ where $\lambda$ is the ultrasound wavelength, Eq. 13 is obtained:

$$p_s(r, \omega) = \frac{2ik^4}{\omega \kappa_0} W_t(\omega) E(\omega) \iiint_{V_0} \qquad \text{Eq. 13}$$

$$\left\{ [\gamma_\kappa(r_0) + \cos(\theta) \gamma_\rho(r_0)] g_0(r \mid r_0) \times \iint_{S_t} g_0(r_0 \mid r') ds' \right\} dv_0,$$

where $\theta$ is the angle between the vector from the center of the transmitting element 16 to the point where the inhomogeneity is located, and the vector from the location of the inhomogeneity to the observation point.

Substituting Eq. 11 yields Eq. 14:

$$p_m(\omega) = \qquad \text{Eq. 14}$$

$$\frac{2ik^4}{\omega \kappa_0} W_t(\omega) E(\omega) W_r(\omega) \iiint_{V_0} \left\{ [\gamma_\kappa(r_0) + \cos(\theta) \gamma_\rho(r_0)] \iint_{S_t} \right.$$

$$\left. g_0(r_0 \mid r', \omega) ds' \iint_{S_r} g_0(r \mid r_0, \omega) ds \right\} dv_0.$$

It is assumed that density fluctuations are much smaller than compressibility fluctuations. Therefore, Eq. 14 can be simplified as $$p_{i,j}(\omega) = \frac{2ik^4}{\omega \kappa_0} E(\omega) F_{i,j}(\omega) \iiint_{V_0} \gamma_\kappa(r_0) a_i(r_0, \omega) a_j(r_0, \omega) dv_0, \qquad \text{Eq. 15}$$

where the subscript i denotes the transmitting element, the subscript j denotes the receiving element, $a_i(r_0,\omega)$ is the integral of the Green's function over the surface of element i given by $$a_i(r_0, \omega) = \iint_{S_i} g_0(r \mid r_0) ds, \qquad \text{Eq. 16}$$

and the electromechanical transfer function $F_{i,j}(\omega)$ is given by:

$$F_{i,j}(\omega) = W_{t_i}(\omega) W_{r_j}(\omega). \qquad \text{Eq. 17}$$

The integration in Eq. 16 accounts for the finite size effects of the ultrasound transducer elements 16 used in the derivation of the inter-element transfer matrix of step 70 in FIG. 4.

With respect to the electro-mechanical parameters 72 of FIG. 4, variations in the sensitivity and time response from element-to-element may be compensated by calibration according to methods known to those skilled in the art.

Integration of the calibration data into the inter-element response matrix is explained as follows. The calibrated spectrum $p_{i,j}^{cal}(\omega)$ is given by Eq. 18:

$$p_{i,j}^{cal}(\omega) = R_i(\omega) R_j(\omega) p_{i,j}(\omega) = \qquad \text{Eq. 18}$$

$$\frac{2ik^4}{\omega \kappa_0} E(\omega) R_i(\omega) R_j(\omega) F_{i,j}(\omega) \iiint_{V_0} \gamma_\kappa(r_0) a_i(r_0) a_j(r_0) dv_0 =$$

$$\frac{2ik^4}{\omega \kappa_0} E(\omega) F(\omega) \iiint_{V_0} \gamma_\kappa(r_0) a_i(r_0) a_j(r_0) dv_0$$

where $p_{i,j}(\omega)$ is the spectrum given by Eq. 15 and $R_i(\omega)$ and $R_j(\omega)$ are the calibration filters for elements i and j, respectively. The function $F(\omega) = R_i(\omega) R_j(\omega) F_{i,j}(\omega)$ is now independent of the subscripts i and j. Using Eq. 18 the inter-element response matrix K is given by Eq. 19:

$$K = \frac{2ik^4}{\omega \kappa_0} F(\omega) \iiint_{V_0} \gamma_\kappa(r_0) A_{r_0} A_{r_0}^T dv_0, \qquad \text{Eq. 19}$$

where the superscript T denotes the transpose and $A_{r_0}$ is an N-dimensional column vector given by $$[a_1(r_0, \omega) a_2(r_0, \omega) \ldots a_N(r_0, \omega)]. \qquad \text{Eq. 20}$$

The expression for the inter-element transfer matrix given by Eq. 19 is used in step 70 shown in FIG. 4, and is more general than that previously derived by other investigators. The generalized expression used in accordance with the present invention incorporates attenuation of the medium, diffraction effects caused by the finite size of the transducer elements, and the sensitivity and time response of the elements.

The behavior of the TR-MUSIC algorithm depends on the coherent point spread function (CPSF) of the ultrasound imaging system. An expression for the CPSF of a linear ultrasound array of N elements is derived. The inter-element transfer matrix K is then used to derive an equation for the time-reversal matrix T at step 80 (see FIG. 4). The matrix T is then used to derive a generalized expression for the pseudo-spectrum 82 of for the generalized TR-MUSIC algorithm 66 of the present invention.

In classical TR imaging, images are formed by back-propagating the waves measured by all elements 16 of the transducer array 14. The back-propagation is performed numerically, assuming the sound speed and the transducer-array 14 geometry are known. The CPSF of a transducer array 14 is the image of a point source obtained using classical TR imaging. The CPSF plays an important role in connection with the lateral and axial resolutions of the TR-MUSIC algorithm. In the following, an equation for the CPSF is derived.

The wavefield at location r that results from a point source at $r_0$ is given by the Green's function $g(r|r_0,\omega)$. Using Eq. 11, the signal measured by element i is $$p_i(\omega) = W_r(\omega) \int\int_{S_r} g_0(r \mid r_0, \omega) ds \qquad \text{Eq. 21}$$
$$= W_{ri}(\omega) a_i(\omega, r_0),$$

where the term $p_s(r,\omega)$ is replaced by $g_0(r|r_0,\omega)$ in Eq. 11. By simultaneously re-emitting the time-reversed measured signals from each transducer element, ultrasound waves are focused back to the location of the point source. In the frequency domain, this operation is equivalent to re-emitting the complex conjugates of the spectra of the measured signals. The CPSF is the sum of the re-emitted fields. Using Eq. 10 and Eq. 21, the CPSF equation Eq. 22 is obtained:

$$CPSF(r \mid r_0, \omega) = \frac{2ik^2}{\omega\kappa_0} \sum_{i=1}^{N} W_{ti}(\omega)[W_{ri}(\omega)a_i(r_0, \omega)]^* a_i(r, \omega) = \qquad \text{Eq. 22}$$
$$\frac{2ik^2}{\omega\kappa_0} \sum_{i=1}^{N} W_{ri}^*(\omega) W_{ti}(\omega) a_i^*(r_0, \omega) a_i(r, \omega)$$

where $E_i(\omega)$ is replaced by $p_i^*(\omega)$ in Eq. 10 and sum over the number of transducer elements 16. An approximate expression for the CPSF is obtained by assuming that the transmit and receive electromechanical responses are equal for all array elements, i.e., $W_{ti}(\omega) = W_t(\omega)$ and $W_{ri}(\omega) = W_r(\omega)$. Therefore, the CPSF is given by $$CPSF(r \mid r_0, \omega) = W_r^*(\omega) W_t(\omega) \sum_{i=1}^{N} a_i^*(r_0, \omega) a_i(r, \omega) \qquad \text{Eq. 23}$$
$$= W_r^*(\omega) W_t(\omega) \langle A_{r_0}, A_r \rangle$$

where the angular brackets denote the inner product in $C^N$, i.e., $$\langle A_{r_0}, A_r \rangle = A_{r_0}^\dagger \cdot A_r \qquad \text{Eq. 24}$$
$$= \sum_{i=1}^{N} a_i^*(r_0, \omega) a_i(r, \omega)$$

The superscript † denotes the conjugate transpose. The CPSF achieves a maximum at the location of a point source, and decays away from the point source. The spatial extent of the CPSF is determined by the size of the elements, the number of elements, the geometry of the transducer array, the location of the point source with respect to the transducer array, and the ultrasound wavelength. Based on this result, two point scatterers located at $r_m$ and $r_{m'}$ are well resolved by the imaging system only if $$\langle A_{r_m'}, A_{r_m} \rangle = \langle A_{r_m}, A_{r_m} \rangle \delta_{m,m'}, \qquad \text{Eq. 25}$$

where δ is the delta function.

The time-reversal matrix T is defined as $$T = K^\dagger K = K^* K, \qquad \text{Eq. 26}$$

where the superscripts † and * denote the adjoint and the complex-conjugate of the matrix, respectively. The second equality follows from the fact that the inter-element transfer matrix K is symmetric. Applying Eq. 19 results in $$T = \frac{-4k^8}{(\omega\kappa_0)^2} |F(\omega)|^2 \int\int\int_{V_0} \int\int\int_{V_0} [\Lambda(r_0, r_0') A_{r_0}^* A_{r_0'}^T] dv_0 dv_0', \qquad \text{Eq. 27}$$

where $$\Lambda(r_0, r_0') = \gamma_k(r_0) \gamma_k(r_0') \langle A_{r_0}, A_{r_0'} \rangle. \qquad \text{Eq. 28}$$

The TR matrix is self-adjoint because $$T^\dagger = [(K^*K)^*]^T = (KK^*)^T = (k^\dagger K^T) = (K^*K) = T, \qquad \text{Eq. 29}$$

and positive semi-definite because for any vector v, we have $$\langle Tv, v \rangle = \langle K^*Kv, v \rangle = \langle Kv, Kv \rangle = \|Kv\|^2 \geq 0. \qquad \text{Eq. 30}$$

It is observed that a positive semi-definite matrix has N non-negative eigenvalues. Indeed if $Tv = \lambda v$ then $\langle Tv, v \rangle = \lambda \|v\|^2 \geq 0$ yielding $\lambda \geq 0$. The eigenfunction associated with the largest eigenvalue of the matrix T specifies an incident wave that maximizes the scattered energy received by the transducer elements. In other words, transmitting the eigenvector associated with the largest eigenvalue focuses energy on the medium inhomogeneities that would result in the maximum scattered energy received by the transducer elements. Other eigenvectors also focus energy on inhomogeneities with and efficiency that is quantified by the associated eigenvalues. In the special case where the medium contains M point scatterers, Eq. 27 becomes $$T = \frac{-4k^8}{(\omega\kappa_0)^2} |F(\omega)|^2 \sum_{m=1}^{M} \sum_{m'=1}^{M} \Lambda_{m,m'} A_{r_m}^* A_{r_m'}^T, \qquad \text{Eq. 31}$$

where $$A_{r_m}^T = [a_1(r_m, \omega) \quad a_2(r_m, \omega) \quad \ldots \quad , a_N(r_N, \omega)] \qquad \text{Eq. 32}$$

and $$\Lambda_{m,m'} = \gamma_k(r_m) \gamma_k(r_{m'}') \langle A_{r_m}, A_{r_m'} \rangle. \qquad \text{Eq. 33}$$

Eq. 31 is the generalized TR matrix detailed in step 80 shown in FIG. 4, and accounts for electromechanical response, variations in element sensitivity, attenuation in the target medium, etc. Note that Eq. 31 is a more general expression for the TR matrix than previously derived by other investigators.

When the number of scatterers M is less than the number of transducer element N, the rank of the matrix T is equal to M. Since the matrix T is self-adjoint and positive semi-definite, the matrix has M eigenvectors with positive non-zero eigenvalues, and (N–M) eigenvectors with zero eigenvalues. In addition, all the eigenvectors are orthogonal; i.e., $$T\mu_m = \lambda_m \mu_m \, m = 1, 2, \ldots, M$$

$$T\mu_{m_0} = 0 \, m_0 = M+1, M+2, \ldots, N$$

$$\langle \mu_m, \mu_{m'} \rangle = \delta_{m,m'}, \qquad \text{Eq. 34}$$

where $\mu_m$ is an eigenvector with nonzero eigenvalue, $\mu_{m_0}$ is an eigenvector with zero eigenvalue, and $\lambda_m$ is a positive eigenvalue. When the scatterers are well resolved, the eigenvectors with non-zero eigenvalues are exactly the vectors $A_{r_m}^*$. When the scatterers are not well resolved by the imaging system, each eigenvector with non-zero eigenvalue is a linear superposition of the vectors $A_{r_m}^*$.

The MUSIC algorithm makes use of the fact that the matrix T is a projection operator into the subspace spanned by the vectors $A_{r_m}^*$. This means that the (N–M) eigenvectors with zero eigenvalues are orthogonal to any linear combination of the vectors $A_{r_m}^*$ i.e., $$\langle \mu_{m_0}, A_{r_m}^* \rangle = \langle \mu_{m_0}^*, A_{r_m} \rangle = 0 \, m=1,2,\ldots,M \; m_0=M+1, M+2,\ldots,N.$$

$$m_0 = M+1, M+2, \ldots, N. \qquad \text{Eq. 35}$$

The MUSIC algorithm for time-reversal imaging is obtained by forming the pseudo-spectrum PS(r) such that:

$$PS(r) = \frac{1}{\sum_{m_0=M+1}^{N} |\langle \mu_{m_0}^*, A_r \rangle|^2}. \qquad \text{Eq. 36}$$

The inner product $\langle \mu_{m_0}^*, A_r \rangle$ will vanish whenever r corresponds to the location of one of the scatterers, and this would occur for well-resolved as well as non-resolved scatterers. Note that under ideal situations when the recorded signals are not corrupted by noise, the pseudo-spectrum will exhibit super-resolution, i.e. the resolution of imaging point scatterers will exceed the resolution dictated by the CPSF. The generalized expression for the pseudo-spectrum (e.g. step 82 in FIG. 4), which is given by Eq. 36 above, accounts for the attenuation in the background medium, and the diffraction effects caused by the finite size of the transducer elements 16.

Windowed TR-MUSIC Algorithm

When the number of scatterers is larger than the number of transducer elements, the eigenvectors of the TR matrix all have nonzero eigenvalues. In this case, the TR-MUSIC imaging algorithm is no longer valid for imaging point scatterers. This problem can also occur if the imaging plane contains numerous extended targets.

Figures 5, 6:
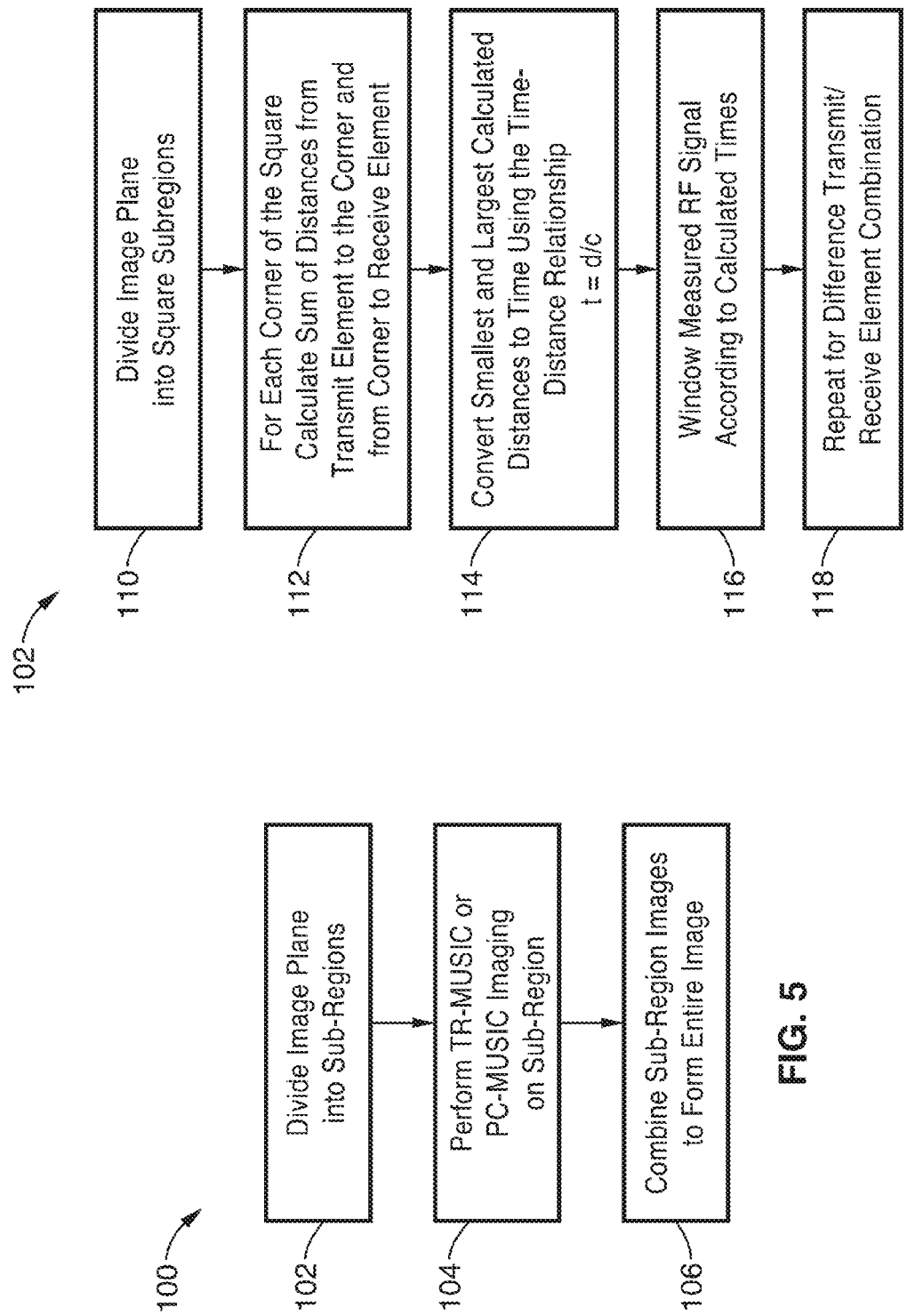
FIG. 5 is a flow diagram of a windowed TR-MUSIC method of the present invention.
FIG. 6 is a flow diagram for dividing the image plane in accordance with the windowed method shown in FIG. 5.
Figure 7B:
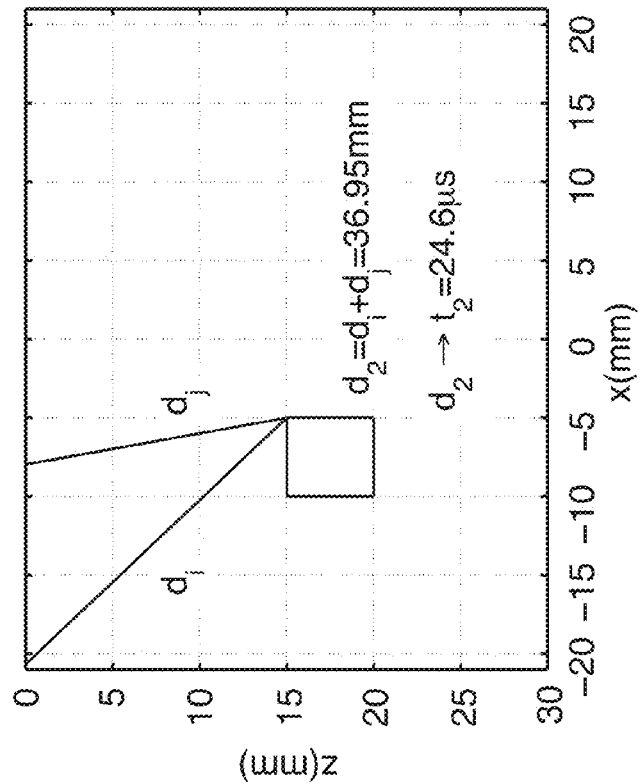
FIG. 7A through FIG. 7D show the distances from a transmitting element and a receiving element to the four corners of a chosen sub-region.
Figure 7A:
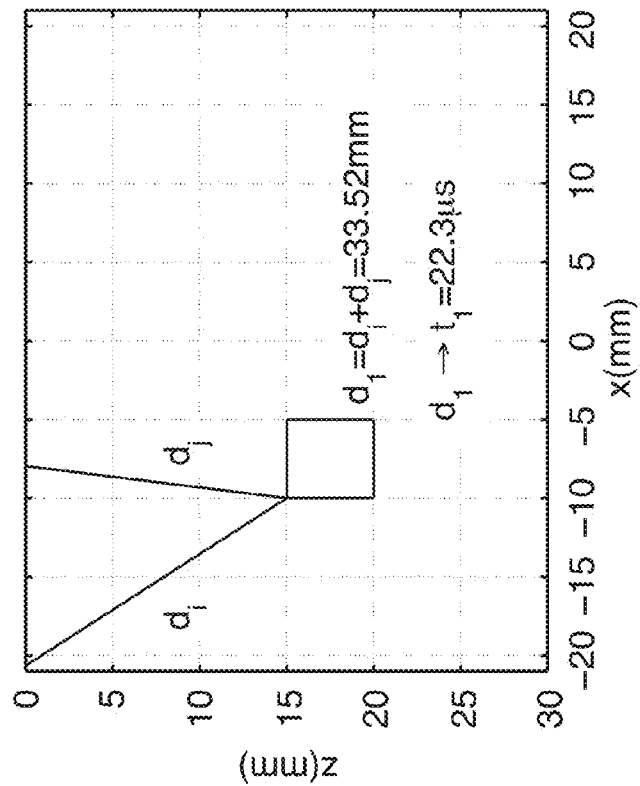
Figure 7D:
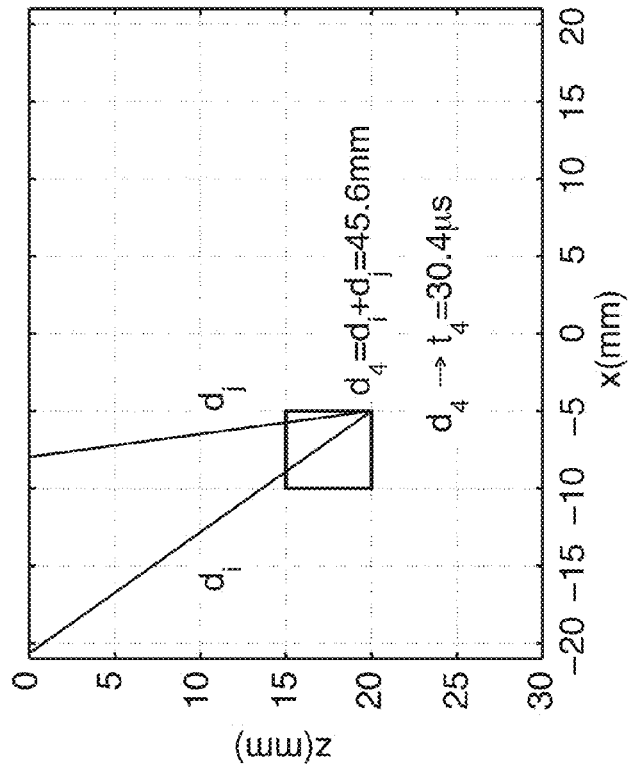
Figure 7C:
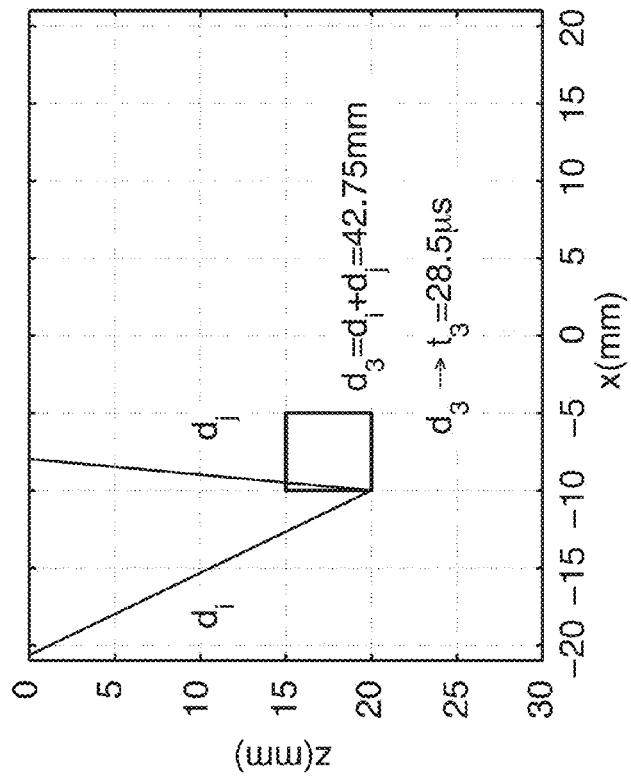

FIG. 5 shows a flow diagram of a windowed TR-MUSIC method 100 of the present invention. The imaging plane is divided into multiple sub-regions at step 102 and then each sub-region is imaged (e.g. via generalized TR-MUSIC method 66 shown in FIG. 4 and detailed above, or modified TR-MUSIC method 150 shown in FIG. 8, or PC MUSIC method 200 of FIG. 13) at step 104. The size of the sub-region in step 102 is chosen such that the number of scatterers within the sub-region is smaller than the number of transducer elements. All the recorded radio-frequency (RF) time signals are windowed such that the time samples of the window correspond to spatial locations of the chosen sub-region. The sub-region images are then combined to form an entire image at step 106.

FIG. 6 is a flow diagram of a preferred embodiment of a method for performing step 102 of the method shown in FIG. 5. FIGS. 7A through 7D illustrate graphically how windowing is performed for a square sub-region as detailed in step 102 of FIG. 5. The image plane is first divided into square sub-regions at step 110. For each corner of the sub-region, the sum of the distance from the corner to the transmitting element and the distance from the corner to the receiving element is computed at step 112, as shown in FIGS. 7A through 7D. At step 114, the times corresponding to the computed distances are calculated. The start and end times of the window are assigned as the times corresponding to the shortest and longest calculated distances (minimum and maximum). The shortest and longest calculated distances are converted to time using the time-distance relationship t=d/c. At step 116, the calculated time window is applied to the measured RF signal, and the time samples outside the window are set to zero. Finally, the process is repeated at step 118 different transmit-receive element combinations.

FIG. 7E shows an example of a measured received signal. FIG. 7F shows the resulting signal after setting the time samples outside the time window to zero.

Referring to step 104 of FIG. 5, to obtain an image of the chosen sub-region, the spectra are first calculated by performing Fast Fourier Transform (FFT) on the windowed signals. The TR matrix is then constructed (e.g., performing step 80 in FIG. 4) at a given frequency and eigenvalue decomposition (EVD) is performed. The image of the chosen sub-region is formed by calculating the pseudo-spectrum given by Eq. 36 (e.g., step 80 in FIG. 4). The images of all the sub-regions are then combined to form the entire image at step 106.

The advantage of this technique is that it allows the computations for forming the different images to be carried out in parallel. Since the emitted ultrasound waves from the transducer elements are unfocused, each windowed signal contains ultrasound waves that originate from an area between two ellipses whose foci are the locations of the transmitting element and the receiving element. Signals that originate from outside the chosen sub-region act as nuisance to the desired signals. However, since N×N time signals are needed to generate the TR matrix, the effects of the undesired signals is minimal due to the effective focusing on the selected sub-region.

The windowed TR-MUSIC method 100 of FIG. 5 may be applied to the generalized TR-MUSIC method 66 of FIG. 4 described above, or the modified TR-MUSIC imaging algorithm 150 of FIG. 8 and PC-MUSIC algorithm 200 of FIG. 13 described below.

TR-MUSIC Algorithm Using Compressibility and Density Contrasts

The TR-MUSIC algorithm, both in its classic form, and in the generalized method 66 shown in FIG. 4, assumes that the point targets 42 have no density contrast with the background medium 44 (see FIG. 2), and that ultrasound scattering is caused only by compressibility contrasts. In FIG. 8, a modified TR-MUSIC imaging algorithm 150 is used to account for ultrasound scattering from both density and compressibility contrasts. In addition, an inversion process was used for estimating density and compressibility contrasts of point scatterers with known locations. These algorithms are valid under the weak scattering (Born) approximation.

The description of the modified TR-MUSIC imaging algorithm 150 is detailed as follows. First, an expression for the inter-element response matrix K for point scatters with density contrasts as well as compressibility contrasts is provided. Next, singular-value decomposition of the matrix K and the MUSIC algorithm are used to form a pseudo-spectrum that peaks at the locations of the point scatterers that may have the density contrast and/or the compressibility contrast relative to the background medium. Then, the matrix K and information about the locations of the point scatterers is used to develop a linear-least-squares method to estimate the density and compressibility contrasts of the point scatterers. Finally, numerical examples are provided to demonstrate the improved capability of the modified TR-MUSIC imaging algorithm 150.

For generating the inter-element response matrix for point scatterers with density and compressibility contrasts, we consider an array of N ultrasound transducer elements interrogating a homogeneous medium containing point scatterers that vary in compressibility and density with respect to the background medium. Each element is excited sequentially and the backscattered signals are measured by all elements, yielding the inter-element response matrix $K_{ij}(\omega)$, with i and j ranging from 1 to N, respectively. We derive an expression for the matrix K as follows. First, we review the equation for the scattered field from an inhomogeneous medium. Then, we consider the transducer model for calculation of the incident field. Finally, we combine the wave-equation solution and the transducer model to give the equation for the recorded electrical signal and form each element of the inter-element response matrix.

The integral equation for the scattered pressure field $p_s(r,\omega)$ from a homogeneous medium containing M point scatterers is given by:

$$p_s(r, \omega) = \sum_{m=1}^{M} \{\underline{k}^2 \gamma_\kappa(r_m) p(r_m, \omega) g_0(r \mid r_m, \omega) - \nabla \cdot [\gamma_\rho(r_m) \nabla p(r_m, \omega)] g_0(r \mid r_m, \omega)\}, \quad \text{Eq. 37}$$

where $\omega$ is the angular frequency, r is the receiver location, $r_m$ is the location of the $m^{th}$ point scatter, $\underline{k}$ is the complex wavenumber, and $g_0$ is the Green's function. The fluctuation functions $\gamma_\kappa$ and $\gamma_\rho$ are the relative compressibility and density differences between the scatterer and the surrounding medium, respectively, given by:

$$\gamma_\kappa(r_m) = \frac{\kappa(r_m) - \kappa_0}{\kappa_0}, \quad \text{Eq. 38}$$

$$\gamma_\rho(r_m) = \frac{\rho(r_m) - \rho_0}{\rho(r_m)}, \quad \text{Eq. 39}$$

where $\rho_0$ is the average or background density, and $\kappa_0$ is the average or background compressibility of the medium. $\gamma_\rho$ is herein defined as the density contrast and $\gamma_\kappa$ as the compressibility contrast.

The complex wavenumber $\underline{k}$ is calculated according to Eq. 40:

$$\underline{k} = \frac{\omega}{c} - i\alpha, \quad \text{Eq. 40}$$

where $k=\omega/c$ is the real wavenumber, $\alpha$ is the amplitude attenuation coefficient of ultrasound, c is the average sound speed, and i is the imaginary unit.

The free-space Green's function $g_0(\omega,r|r_0)$ is given by:

$$g_0(r \mid r_m) = \frac{\exp\{-i\underline{k}|r - r_m|\}}{4\pi|r - r_m|}. \quad \text{Eq. 41}$$

Because the wavenumber $\underline{k}$ is complex, the Green's function accounts for the ultrasound attenuation in the medium.

The ultrasound incident field is generated by an ultrasound transducer element, assuming no other sources exist in the medium. In the classical theory of sound in a fluid that exhibits viscous loss, the pressure phasor is given by:

$$p_{inc}(r, \omega) = \frac{i\underline{k}^2}{\omega\kappa_0} W_t(\omega) E(\omega) \int\int_{S_t} \frac{\exp(-i\underline{k}|r - r_0|)}{2\pi|r - r_0|} ds_0, \quad \text{Eq. 42}$$

where the integral is evaluated over the surface of the transmitting element $S_t$, $W_t(\omega)$ is the electromechanical transfer function of the transmitter, and $E(\omega)$ is the input-voltage transfer function. In Eq. 42, it is assumed that the acoustic velocity distribution is constant over the area $S_t$.

The spectrum of the electrical signal measured by the receiving transducer element is given by:

$$p_m(\omega) = W_r(\omega) \int\int_{S_r} p_s(r, \omega) ds, \quad \text{Eq. 43}$$

where the integral is evaluated over the receiving-element 16 area $S_r$, and $W_r(\omega)$ is the electro-mechanical transfer function of the receiver. In Eq. 43, it is assumed that the spatial sensitivity of the detector 12 (FIG. 1) is constant across the area $S_r$. Using this assumption, we incorporate the sensitivity of the detector 12 into $W_r(\omega)$.

When the magnitudes of $\gamma_\rho$ and $\gamma_\kappa$ are small, the Born approximation is valid and the scattered wave from Eq. 38 becomes $$p_s(r, \omega) = \sum_{m=1}^{M} \{\underline{k}^2 \gamma_\kappa(r_m) p_{inc}(r_m, \omega) g_0(r \mid r_m, \omega) - \nabla \cdot [\gamma_\rho(r_m) \nabla p_{inc}(r_m, \omega)] g_0(r \mid r_m, \omega)\}, \quad \text{Eq. 44}$$

where we replace the pressure field $p(r_m,\omega)$ by the incident field $p_{inc}(r_m,\omega)$ on the right-hand side of Eq. (1).

By substituting Eq. 42 into Eq. 44, and assuming that the scatterers are sufficiently far from the transducer element, such that $|r-r_m|>>\lambda$ where $\lambda$ is the ultrasound wavelength, we obtain:

$$p_s(r, \omega) = \frac{2i\underline{k}^4}{\omega\kappa_0} W_t(\omega) E(\omega) \sum_{m=1}^{M} \left\{ [\gamma_\kappa(r_m) + \cos(\theta_m)\gamma_\rho(r_m)] g_0(r \mid r_m) \int\int_{S_t} g_0(r_m \mid r') ds' \right\}. \quad \text{Eq. 45}$$

where $\theta_m$ is the angle between the vector from the center of the transmitting element to the point where the $m^{th}$ scatterer is located, and the vector from the location of the scatterer to the observation point.

Substituting Eq. 45 into Eq. 43 yields the spectrum of the measured signal given by:

$$p_{i,j}(\omega) = F(\omega) \sum_{m=1}^{M} \{[\gamma_\kappa(r_m) + \cos(\theta_{m_{i,j}})\gamma_\rho(r_m)] a_i(r_m, \omega) a_j(r_m, \omega)\}, \quad \text{Eq. 46}$$

where the subscript i denotes the transmitting element, the subscript j denotes the receiving element, $a_i(r_m,\omega)$ is the integral of the Green's function over the surface of element i given by:

$$a_i(r_m) = \iint_{S_i} g_0(r \mid r_m) ds,\qquad \text{Eq. 47}$$

and $F(\omega)$ takes into account the transfer function of the transmit pulse and the electromechanical response, that is, $$F(\omega) = \frac{2ik^4}{\omega \kappa_0} E(\omega) W_t(\omega) W_r(\omega),\qquad \text{Eq. 48}$$

where it is assumed that the transmit and receive electromechanical responses are the same for all ultrasound transducer elements, i.e., $W_{t_i}(\omega) = W_t(\omega)$ and $W_{r_j}(\omega) = W_r(\omega)$.

Variations in the element-to-element sensitivity and the time response can be compensated using a calibration method. Based on Eq. 46, the response matrix K can be written as:

$$K = F(\omega) \sum_{m=1}^{M} \gamma_\kappa(r_m) \begin{bmatrix} a_1(r_m)a_1(r_m) & a_1(r_m)a_2(r_m) & \cdots & a_1(r_m)a_N(r_m) \\ a_2(r_m)a_1(r_m) & a_2(r_m)a_2(r_m) & \cdots & a_2(r_m)a_N(r_m) \\ \vdots & \vdots & \vdots & \vdots \\ a_N(r_m)a_1(r_m) & a_N(r_m)a_2(r_m) & \cdots & a_N(r_m)a_N(r_m) \end{bmatrix} +$$

$$\gamma_\rho(r_m) \begin{bmatrix} \cos(\theta_{m_{1,1}})a_1(r_m)a_1(r_m) & \cos(\theta_{m_{1,2}})a_1(r_m)a_2(r_m) & \cdots & \cos(\theta_{m_{1,N}})a_1(r_m)a_N(r_m) \\ \cos(\theta_{m_{2,1}})a_2(r_m)a_1(r_m) & \cos(\theta_{m_{2,2}})a_2(r_m)a_2(r_m) & \cdots & \cos(\theta_{m_{2,N}})a_2(r_m)a_N(r_m) \\ \vdots & \vdots & \vdots & \vdots \\ \cos(\theta_{m_{N,1}})a_N(r_m)a_1(r_m) & \cos(\theta_{m_{N,2}})a_N(r_m)a_2(r_m) & \cdots & \cos(\theta_{m_{N,N}})a_N(r_m)a_N(r_m) \end{bmatrix} =$$

$$F(\omega) \sum_{m=1}^{M} \gamma_\kappa(r_m) A(r_m) A^T(r_m) \gamma_\rho(r_m) [\ B_1(r_m)\ \ B_2(r_m)\ \ B_N(r_m)\ ],\qquad \text{Eq. 49}$$

where the vectors $A(r_m)$ and $B_n(r_m)$ are given by $$A^T(r_m) = [a_1(r_m) a_2(r_m) \ldots a_N(r_m)],\qquad \text{Eq. 50}$$

and $$B_n^T(r_m) = [\cos(\theta_{m_{1,n}})a_1(r_m)a_n(r_m)\cos(\theta_{m_{2,n}})a_2(r_m)\\ a_n(r_m) \ldots \cos(\theta_{m_{N,n}})a_N(r_m)a_N(r_m)],\qquad \text{Eq. 51}$$

where the superscript T denotes the transpose of the vector.

The inter-element response matrix given by Eq. 49 is more general than classic TR MUSIC. Eq. 49 incorporates the density and compressibility contrasts of the scatterers, ultrasound attenuation in the medium, diffraction effects caused by the finite size of the transducer elements, and the sensitivity and time response of the transducer elements. Derivation of Eq. 49 is also further detailed below with respect to FIG. 8. It should be noted that the matrix K in Eq. 49 is symmetric.

FIG. 8 shows a flow diagram of a modified TR-MUSIC imaging algorithm 150 that generates an expression for the inter-element response matrix K for point scatters with density contrasts as well as compressibility contrasts, in accordance with Eq. 49 above. Note that FIG. 8 builds upon the method 66 shown in FIG. 4, where like reference numbers denote like steps.

Initially, the compressibility contrast $\gamma_\rho$ and density contrast $\gamma_\kappa$ are not known. Accordingly, the method first generates an inter-element transfer matrix at step 70 that incorporates the electro-mechanical response 72 of each element 16 in the array 14, the diffraction impulse response 74 of each element 16, and the attenuation 76 in the medium 44, as shown in generalized method 66 of FIG. 4. Next, at step 80, the generalized time-reversal (TR) matrix is generated. Finally, a pseudo-spectrum for generalized TR-Music imaging is generated at step 82. At step 152, the generalized pseudo-spectrum 82 from step 82 and locations of the point scatterers are then applied with an inversion method to estimate the density and compressibility contrasts of the point scatterers at step 154 to generate the inter-element response matrix K at step 156 for point scatters with density contrasts as well as compressibility contrasts, in accordance with Eq. 49.

In particular, the matrix K maps $C^n$, the vector space of complex N-tuples, to the subspace $S_0$ spanned by the vectors $A(r_m)$ and $B_n(r_m)$, i.e., $$S_0 = \text{Span}\{A(r_m), B_n(r_m), m=1,2,\ldots,M\ n=1,2,\ldots,N\}.\qquad \text{Eq. 52}$$

The rank of the matrix K depends on the number of point targets in the imaging region and the ratio of the density contrast to the compressibility contrast of the point targets. For a single point target, the rank of the matrix K can be up to four. When the density contrast is equal to zero and M<N, the rank of the matrix K is equal to M and the vectors $A(r_m)$ form a basis for $S_0$.

The TR-MUSIC method is based on the singular-value decomposition (SVD) of the K matrix in the form:

$$Kv_p = \sigma_p u_p,\qquad \text{Eq. 53}$$

$$K^\dagger u_p = \sigma_p v_p,$$

$$K = \sum_{p=1}^{N} \sigma_p u_p v_p^\dagger,$$

where superscript † denotes the transpose of the complex conjugate of a vector or a matrix, $\sigma_p$ are the singular values, and $u_p$ and $v_p$ are the left and right singular vectors, respectively. It follows from Eq. 53 that:

$$S_0 = \text{Span}\{u_p, \sigma_p > 0\} \perp \mathcal{N}_0 = \text{Span}\{u_p, \sigma_p = 0\}.\qquad \text{Eq. 54}$$

From Eq. 52 and Eq. 54, it can be seen that the noise eigenvectors $u_p$ belonging to $\mathcal{N}_0$ are orthogonal to the vectors $A(r_m)$ and $B_n(r_m)$, i.e., $u_p^\dagger A(r_m)=0, u_p^\dagger B_n(r_m)=0, \sigma_p=0 \; n=1,2,\ldots,N.$   Eq. 55

The locations of the scatterers can be determined from the time-reversal MUSIC pseudo-spectrum generated by step 82 given by:

$$\Phi(r) = \frac{1}{\sum_{\sigma_p=0} |u_p^\dagger A(r)|^2} + \frac{1}{\sum_{\sigma_p=0} \sum_{n=1}^{N} |u_p^\dagger B_n(r)|^2}$$   Eq. 56 which will peak ideally to infinity when $r=r_m$. Therefore, within the Born approximation, locating the point targets is achieved by finding the maxima of the pseudo-spectrum given by Eq. 56.

Because the inter-element response matrix K is symmetric, it follows that $v_P = u_p^*$, and the pseudo-spectrum can be written in an alternative form:

$$\Phi(r) = \frac{1}{\sum_{\sigma_p=0} |v_p^T A(r)|^2} + \frac{1}{\sum_{\sigma_p=0} \sum_{n=1}^{N} |v_p^T B_n(r)|^2}.$$   Eq. 57

Note that the TR-MUSIC method would fail if the noise subspace $\mathcal{N}_0 = \text{Span}\{u_p, \sigma_p = 0\}$ is empty. This would occur if the rank of the matrix K is equal to the number of transceivers N. When the point targets have a zero-density contrast, the matrix K would have full rank if M≥N. When the targets have both the density and compressibility contrasts, the matrix K can have full rank even if the number of targets is fewer than the number of transceivers.

Referring again to step 152 in FIG. 8, if the locations of the point targets are known and in the absence of density contrast, the scattering strength (compressibility contrast) and the density contrasts of the point targets of can be calculated by finding the least squares solution of an over determined system generated from Eq. 49.

The inter-element response matrix given by Eq. 49 may be regarded as a matrix equation relating the unknown coefficients $\gamma_\kappa(r_m)$ and $\gamma_\rho(r_m)$ to the elements of the matrix $K_{i,j}$ expressed as a vector with $N^2$ elements as follows:

$$\overset{N^2 \times 1}{[K_{i,j}]} = \overset{N^2 \times 2M}{[a_i(r_m)a_j(r_m) \quad \cos(\theta_{m_{i,j}})a_i(r_m)a_j(r_m)]} \overset{2M \times 1}{\begin{bmatrix} \gamma_\kappa(r_m) \\ \gamma_\rho(r_m) \end{bmatrix}},$$   Eq. 58 where:

$[K_{i,j}] = [K_{1,1}, K_{1,2}, \ldots, K_{N,N}]^T,$ $[\gamma_\kappa(r_m)] = [\gamma_\kappa(r_1), \gamma_\kappa(r_2)], \ldots, \gamma_\kappa(r_M)],$ $[\gamma_\rho(r_m)] = [\gamma_\rho(r_1), \gamma_\rho(r_2)], \ldots, \gamma_\rho(r_M)],$ $$[a_i(r_m)a_j(r_m)] = \begin{bmatrix} a_1(r_1)a_1(r_1) & \cdots & a_1(r_M)a_1(r_M) \\ a_1(r_1)a_2(r_1) & \cdots & a_1(r_M)a_2(r_M) \\ \vdots & \vdots & \vdots \\ a_N(r_1)a_N(r_1) & \cdots & a_N(r_M)a_N(r_M) \end{bmatrix},$$

and $[\cos(\theta_{m_{i,j}})a_i(r_m)a_j(r_m)] =$

-continued $$\begin{bmatrix} \cos(\theta_{1_{1,1}})a_1(r_1)a_1(r_1) & \cdots & \cos(\theta_{M_{1,1}})a_1(r_M)a_1(r_M) \\ \cos(\theta_{1_{1,2}})a_1(r_1)a_2(r_1) & \cdots & \cos(\theta_{M_{1,2}})a_1(r_M)a_2(r_M) \\ \vdots & \vdots & \vdots \\ \cos(\theta_{1_{N,N}})a_N(r_1)a_N(r_1) & \cdots & \cos(\theta_{M_{N,N}})a_N(r_M)a_N(r_M) \end{bmatrix}.$$

If the locations of the point targets are known (e.g., via the pseudo-spectrum generated at step 82, a linear least squares solution of the over determined system at step 152 given by Eq. 58 yields the coefficients $\gamma_\kappa(r_m)$ and $\gamma_\rho(r_m)$ at step 154. The locations of the point targets can be determined using the modified TR-MUSIC algorithm. Note that we neglected the electromechanical response function $F(\omega)$ in Eq. 58. Therefore, exact estimates of $\gamma_\kappa(r_m)$ and $\gamma_\rho(r_m)$ are be obtained if the scaling factor $F(\omega)$ is known in advance.

Referring still to FIG. 8, data from the density and compressibility contrasts at step 154 are then used to generate the inter-element response matrix K at step 156 for point scatters with density contrasts and compressibility contrasts per Eq. 49. The time reversal matrix is then calculated at step 158 to generate the pseudo spectrum with density and compressibility contrasts at step 160.

Referring now to FIG. 9A through FIG. 12B, numerical simulations were performed to validate the modified TR-MUSIC algorithm 150 for imaging point scatterers with density and compressibility contrasts, and compare the results with those obtained using the classic (non-generalized) TR-MUSIC algorithm. The effect of ultrasound noise on the image resolution and the accuracy of target localization was studied. In addition, the accuracy in the estimates of point targets' compressibility and density contrasts were evaluated under noise conditions and different ratios of the density contrast to the compressibility contrast ($\gamma_\rho/\gamma_\kappa$).

For these experiments, a linear ultrasound transducer array 14, as shown in exemplary form in FIG. 1, is simulated such that each element 16 is excited sequentially and the scattered signals 32 are measured by all elements 16 of the array 14 (see FIG. 2). Ultrasound signals 32 scattered from a number of point targets 42 distributed in a homogeneous medium 44 with an ultrasound attenuation coefficient of 0.5 dB/cm-MHz and a sound speed of 1540 m/s were obtained. The array 14 comprised 128 elements. For each element 16, the azimuthal length of was 300 μm, the elevation length was 6 mm, and the pitch was 325 μm. The center frequency of each element 16 was 7.5 MHz and the 6-dB fractional bandwidth was 65%.

Eq. 46 was used to calculate ultrasound scattered signals. Given the sound speed of the medium and the complex wavenumber $\underline{k}$, the double integrals of Eq. 11 were numerically evaluated over the surfaces of the transducer elements 16. The electromechanical transfer functions $W_t(\omega)$ and $W_r(\omega)$ were each approximated by the spectrum obtained by performing FFT on a Gaussian-modulated sinusoidal pulse with a center frequency of 7.5 MHz and a 6 dB fractional bandwidth. Time zero of the Gaussian-modulated sinusoidal pulse corresponds to the time where the leading pulse envelope falls to 60 dB. The time-dependent signals are calculated using the inverse FFT of the spectra obtained using Eq. 46.

To compare the image resolution obtained with the modified TR-MUSIC algorithm 150 of the present invention to that obtained with the classic (non-generalized) TR-MUSIC algorithm, several cases of ultrasound scattering from two point targets separated laterally by λ/2, λ/4, or λ/8 were simulated, where λ is the ultrasound wavelength of the scanner 12. The midpoint between the two targets was located 2.5 cm axially from the center of the transducer array 14. In all cases, the compressibility contrast $\gamma_\kappa$ of the two point targets was fixed at 0.05. The density contrast $\gamma_\rho$ of the two point targets was varied such that $\gamma_\rho/\gamma_\kappa=1/16$, 1/8, ..., 8,16.

In all simulated cases, it was found that there is a clear cutoff between the signal and noise singular values of the inter-element response matrix. Eq. 56 was used to calculate the pseudo-spectrum of the modified TR-MUSIC algorithm 150 (e.g. in accordance with step 160 shown in FIG. 8). The pseudo-spectrum of the original TR-MUSIC algorithm by ignoring the second term of Eq. 56. Note that attenuation and diffraction effects are compensated during the calculations of the vectors A(r) and, B(r).

Figure 9A:
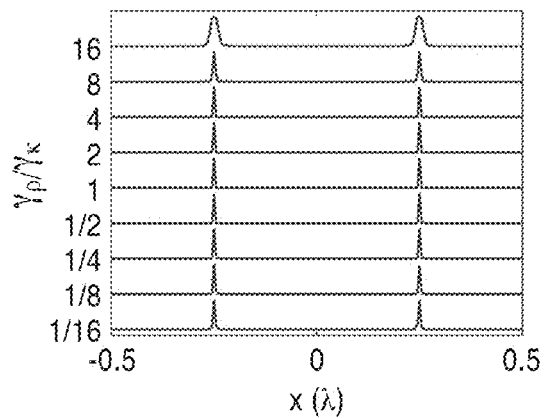
FIG. 9A through FIG. 9F are plots of lateral profiles Z=25 mm for the noise-free pseudo-spectra calculated using the original TR-MUSIC algorithm for two point targets separated laterally by $\lambda/2$ (FIG. 9A), $\lambda/4$ (FIG. 9C), and $\lambda/8$ (FIG. 9E).
Figure 9B:
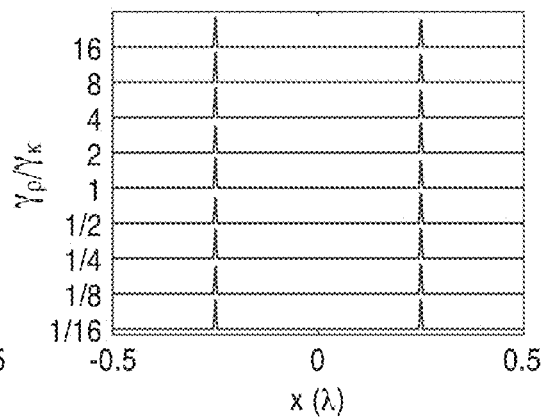
Figure 9C:
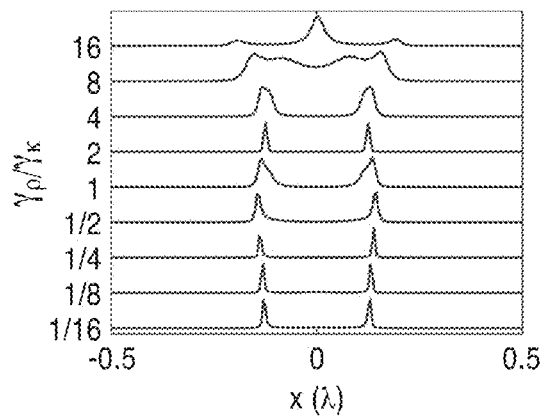
Figure 9D:
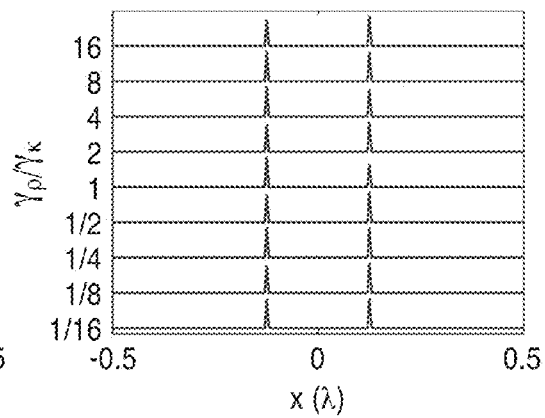
Figure 9E:
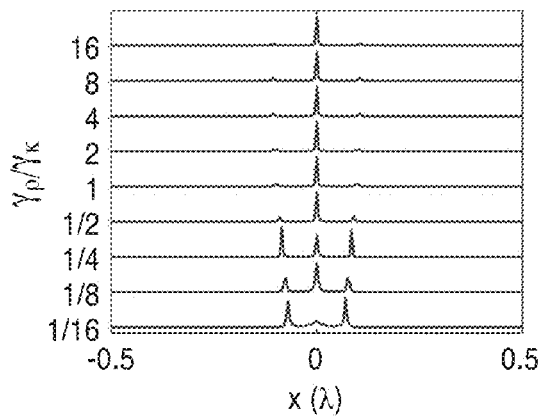
Figure 9F:
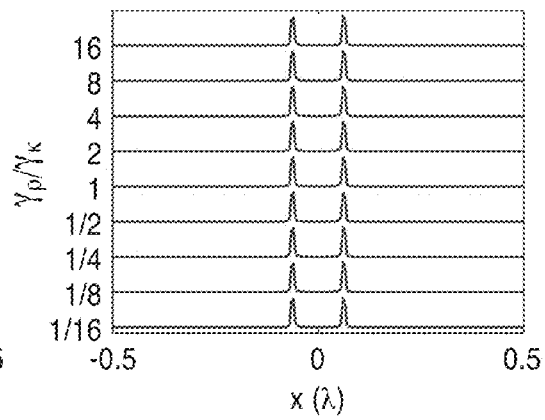

FIG. 9A, FIG. 9C, and FIG. 9E show lateral profiles at Z=25 mm for the noise-free pseudo-spectra calculated using the original TR-MUSIC algorithm for two point targets separated by λ/2, λ/4, and λ/8, respectively. FIG. 9B, FIG. 9D, and FIG. 9F show the profiles when the pseudo-spectra are calculated using the modified TR-MUSIC algorithm 150 of the present invention. When the separation is λ/2, the two point targets are well resolved and accurately located with both algorithms and for all simulated values of $\gamma_\rho/\gamma_\kappa$. When the separation is λ/4, the original TR-MUSIC algorithm fails to resolve the point targets when $\gamma_\rho/\gamma_\kappa>4$. When the separation is λ/8, it was observed that peaks that do not correspond to the locations of the targets, and only targets that have $\gamma_\rho/\gamma_\kappa<1/4$, are resolved. The results of FIG. 9A through FIG. 9F demonstrate that the modified TR-MUSIC algorithm 150 of the present invention gives significantly higher image resolution compared to the original TR-MUSIC algorithm. The improvement of the image resolution is particularly significant when the target separation is small and the ratio of the density contrast to the compressibility contrast is large.

The TR-MUSIC imaging results in FIG. 9A through FIG. 9F were obtained under a noise-free condition. The effect of noise on image resolution was also tested by adding zero-mean Gaussian noise to the inter-element response matrix K and calculating the pseudo-spectrum of the modified TR-MUSIC algorithm 150 according to Eq. 56. The signal-to-noise ratio was defined as:

$$SNR = 20\log_{10}\left(\frac{\|K\|}{\|N\|}\right), S \quad \text{EQ. 59}$$

where N is the noise matrix and ∥ ∥ denotes the norm of the matrix. FIG. 10A through FIG. 10D show lateral profiles of the normalized pseudo-spectra of two point targets separated laterally by λ/2 when the SNR is 5 dB (FIG. 10A), 15 dB (FIG. 10B), 25 dB (FIG. 10C), and 35 dB (FIG. 10D), respectively. Both point targets have $\gamma_\rho/\gamma_\kappa=1$. It is clear from FIG. 10A through FIG. 10D that the image resolution decreases with decreasing SNR; hence, the super-resolution capability of modified TR-MUSIC imaging method 150 decreases under low SNRs.

Referring now to FIG. 11A and FIG. 11B, several cases of ultrasound scattering from a point target were simulated to test the accuracy in the estimates of $\gamma_\kappa$ and $\gamma_\rho$ calculated using the step 156 shown in FIG. 8. The target was located 2.5 cm axially from the center of the transducer array 14. The effect of SNR on the accuracy of the estimates was first studied. $\gamma_\rho/\gamma_\kappa=1$ was set, and the SNR was varied from 0 dB to 50 dB, with an increment of 5 dB. For a given value of SNR, thirty realizations of noise were obtained and added to the matrix K. $\gamma_\kappa$ and $\gamma_\rho$ were estimated for each realization of noise. FIG. 11A shows the relative root-mean-squared (RMS) errors in $\gamma_\kappa$ and $\gamma_\rho$ versus the SNR. As expected, the error decreases with increasing SNR.

Next, the effect of the ratio of the density contrast to the compressibility contrast $\gamma_\rho/\gamma_\kappa$ on the accuracy of the estimates of $\gamma_\kappa$ and $\gamma_\rho$ was investigated. The SNR was fixed at 25 dB and $\gamma_\rho/\gamma_\kappa$ was varied. For each case, thirty realizations of noise were obtained and added to the matrix K. FIG. 11B shows the relative RMS errors in $\gamma_\kappa$ and $\gamma_\rho$ versus $\gamma_\rho/\gamma_\kappa$. The relative RMS error in $\gamma_\rho$ is much higher than that of $\gamma_\kappa$ for low values of $\gamma_\rho/\gamma_\kappa$, and vice versa.

In the simulations presented thus far, all the scattering targets have the same compressibility contrast and the same density contrast. Ultrasound scattering was also performed for five point targets, for which the values of $\gamma_\kappa$ and $\gamma_\rho$ were assigned values between 0 and 0.05. The five targets were randomly distributed in a 10λ×10λ% square sub-region centered 2.5 cm axially from the center of the transducer array 14. The values for $\gamma_\kappa$ and $\gamma_\rho$ are given in Table I. Noise was added to the inter-element response matrix such that the SNR is 25 dB.

Referring to FIG. 12A and FIG. 12B, two images of the point targets were obtained, one (FIG. 12A) using the original TR-MUSIC algorithm, and the other (FIG. 12B) using the modified TR-MUSIC algorithm 150 of the present invention. The images were formed by calculating the logarithm of the pseudo-spectra given by Eq. 56. The dynamic range of the images is 80 dB.

As illustrated in FIG. 12A, it is clear that all the targets are accurately located with the modified TR-MUSIC algorithm 150. However, the original TR-MUSIC algorithm failed to detect Target 3. Looking at Table I, we find that the compressibility contrast of Target 3 is close to zero, which explains why the target was not detected by the original TR-MUSIC algorithm. Note that Target 2 has density contrast that is close to zero, and it is detected with both the original and the new TR-MUSIC algorithms.

After the five point targets are accurately located with modified TR-MUSIC algorithm 150, Eq. 58 was solved to estimate the values of $\gamma_\kappa$ and $\gamma_\rho$ in accordance with step 152 and 154 of FIG. 8. Table I shows the estimated values and the relative error in the estimates. For this simulation with an SNR of 25 dB, the absolute values of the relative errors (RE) in the estimates are less than 5% for Targets 1, 4, and 5. For Target 2, the RE in the estimate of $\gamma_\rho$ is 30%, while the RE in the estimate of $\gamma_\kappa$ for Target 3 is 36%. This result is caused by the low values of $\gamma_\rho$ and $\gamma_\kappa$ for Targets 2 and 3, respectively.

Phase Coherent (PC)-MUSIC Algorithm with Compensation of Phase Response of Transducers In the case of noisy data, the super-resolution property of TR-MUSIC is diminished. Phase-coherent MUSIC (PC-MUSIC), which produces a pseudo-spectrum that retains phase information, reduces noise effects by averaging pseudo-spectra calculated at different frequencies. However, since PC-MUSIC uses phase information, the phase response of ultrasound transducer elements must ideally be taken into account for the algorithm to achieve super resolution and accurate target localization. The phase response of transducer elements, which may not be known beforehand, combines the electro-mechanical and transmitted-pulse phase responses.

Referring to FIG. 13, PC-MUSIC imaging algorithm 200 with compensation for phase response is disclosed. An experimental method was also developed to estimate this response using a glass micro-sphere (smaller than ultrasound wavelength) embedded in a tissue-mimicking phantom with a homogeneous background medium and a known sound speed. It was also demonstrated that the maximum resolution achieved by the phase-coherent TR-MUSIC is limited by the transducer bandwidth and the signal-to-noise ratio.

The description of the PC-MUSIC imaging algorithm 200 with compensation for phase response is detailed as follows. First, the derivation of PC-MUSIC is reviewed. Some numerical examples are provided to demonstrate the importance of compensating for the phase response of transducer elements. An experimental method for estimating phase response is also detailed. Finally, tissue-mimicking phantom images obtained with different imaging modalities, including X-ray mammography, synthetic-aperture ultrasound imaging, classic TR-MUSIC, and PC-MUSIC were compared.

Referring back to FIG. 2, the following PC MUSIC methodology is considered with respect to an array 14 of N ultrasound transducer elements 16 interrogating a medium 44 containing M point scatterers 42. Each transducer element 16 is excited sequentially and the backscattered signals 32 are measured by all elements (see FIG. 3), yielding the inter-element response matrix $K_{ij}(\omega)$ of the array at the angular frequency $\omega$, with subscripts i and j ranging from 1 to N. Under the Born approximation, the matrix K is given by:

$$K = |F(\omega)|e^{i\phi(\omega)} \sum_{m=1}^{M} \gamma_\kappa(r_m)G(r_m, \omega)G^T(r_m, \omega) \quad \text{Eq. 60}$$

$$= |F(\omega)| \sum_{m=1}^{M} \gamma_\kappa(r_m)\left(G(r_m, \omega)e^{\frac{i\phi(\omega)}{2}}\right)\left(G(r_m, \omega)e^{\frac{i\phi(\omega)}{2}}\right)^T,$$

where $F(\omega)$ combines the transfer function of the emitted pulse and the electromechanical responses of the transducer elements, assuming all elements have the same characteristics.

The phase response of $F(\omega)$, $\varphi(\omega)$, is not taken into account in the previous derivation of the PC-MUSIC. The fluctuation function $\gamma_\kappa(r_m)$ is a measure of the relative differences in compressibility between the scatterers and the surrounding background medium. The density fluctuations are assumed to be negligible. In the case of uniformly excited planar transducer elements, the elements of the vector $G_{r_m}$ are the integrals of the Green's function over the surfaces of the transducer element:

$$G^T(r_m, \omega) = \left[\iint_{S_1}\frac{\exp[-i\underline{k}|r_m - r'|]}{4\pi|r_m - r'|}ds', \quad \text{Eq. 61}$$

$$\dots, \iint_{S_N}\frac{\exp[-i\underline{k}|r_m - r'|]}{4\pi|r_m - r'|}ds'\right]$$

where $S_j$ is the surface area of the $j^{th}$ element, $$\underline{k} = \frac{\omega}{c} - i\alpha$$

is the complex wavenumber, $\alpha$ is the amplitude attenuation coefficient of the medium, c is the background sound speed, and i is the imaginary unit.

It is clear that the matrix K is symmetric and maps $C^n$, the vector space of complex N-tuples, to the subspace $S_0$ spanned by the vectors $$G(r_m, \omega)e^{\frac{i\phi(\omega)}{2}}, \text{i.e.,} \quad \text{Eq. 62}$$

$$S_0 = \text{Span}\left\{G(r_m, \omega)e^{\frac{i\phi(\omega)}{2}}, m = 1,2,\dots, M\right\}.$$

The MUSIC algorithm is uses singular-value decomposition (SVD) of the matrix K that can be written in the form:

$$Kv_p = \sigma_p u_p, \quad \text{Eq. 63}$$

$$K^\dagger u_p = \sigma_p v_p,$$

$$K = \sum_{p=1}^{N} \sigma_p u_p v_p^\dagger,$$

where the superscript † denotes the transpose of the complex conjugate of a vector or a matrix, $\sigma_p$ are the singular values, and $u_p$ and $v_p$ are the left and right singular vectors, respectively.

When the scatterers are fully resolved by the imaging system and when M<N, the vectors $G(r_m,\omega)$ evaluated at the scatterer locations form a basis for $S_0$. Under these conditions, the signal singular vectors (vectors with non-zero singular values) can be represented in matrix form as:

$$U_{sig}(\omega) = [u_1 \; u_2 \; \dots \; u_M] = e^{\frac{i\phi(\omega)}{2}} \quad \text{Eq. 64}$$

$$\left[\frac{G(r_1, \omega)}{\|G(r_1, \omega)\|}e^{j\theta_1} \; \frac{G(r_2, \omega)}{\|G(r_1, \omega)\|}e^{j\theta_2} \; \dots \; \frac{G(r_M, \omega)}{\|G(r_M, \omega)\|}e^{j\theta_M}\right],$$

$$V_{sig}(\omega) = [v_1 \; v_2 \; \dots \; v_M] = e^{\frac{-i\phi(\omega)}{2}}\left[\frac{G^*(r_1, \omega)}{\|G(r_1, \omega)\|}e^{j\theta_1}\right.$$

$$\left.\frac{G^*(r_2, \omega)}{\|G(r_2, \omega)\|}e^{j\theta_2} \; \dots \; \frac{G^*(r_M, \omega)}{\|G(r_M, \omega)\|}e^{j\theta_M}\right],$$

where the superscript "*" denotes the complex conjugate.

Since the inter-element response matrix K is symmetric, it follows that $v_p = u_p^*$. However, the SVD analysis of a complex-valued matrix is non-unique by an arbitrary phase, which is the same for the corresponding left and right singular vectors. The phase angles $\theta_m$ in Eq. (6) represent this non-uniqueness.

Ignoring the leading phase term $$e^{\frac{i\phi(\omega)}{2}},$$

the PC-MUSIC algorithm without phase response is based on the pseudo-spectrum given by $$P(r, \omega) = \frac{1}{1 - \sum_{\Delta\omega} A(r, \omega)}, \quad \text{Eq. 65}$$

where

-continued $$A(r, \omega) = \frac{G^H(r, \omega)U_{sig}(\omega)V_{sig}^H(\omega)G^*(r, \omega)}{\|G(r, \omega)\|^2},$$ Eq. 66 and $\Delta\omega$ is a frequency band.

In classic TR-MUSIC, the operator A can be calculated using either the matrix $U_{sig}$ or the matrix $V_{sig}$ as follows:

$$A_U(r, \omega) = \frac{G^H(r, \omega)U_{sig}(\omega)U_{sig}^H(\omega)G(r, \omega)}{\|G(r, \omega)\|^2},$$ Eq. 67

$$A_V(r, \omega) = \frac{G^T(r, \omega)V_{sig}(\omega)V_{sig}^H(\omega)G^*(r, \omega)}{\|G(r, \omega)\|^2}.$$

The operator A of PC-MUSIC retains the phase information, whereas TR-MUSIC does not. In the case of noise-free data, the arbitrary phase angles $\theta_m$ cancel out, and the pseudo-spectrum peaks at the true locations of the scatterers. This occurs even when the scatterers are not resolved by the imaging system, leading to the super-resolution capability of TR-MUSIC. In the case of noisy data, the angles $\theta_m$ cancel out, but operator A has a random phase at each frequency. The improvement in resolution obtained with PC-MUSIC is a result of averaging these random phases over a given frequency band. However, in experimental studies using the formulation of PC-MUSIC given by Eqs. 65 and 66, it was found that the targets are not accurately located, and that the improvement in resolution over TR-MUSIC is minimal.

This is believed to be caused by ignoring the phase factor $$e^{\frac{i\phi(\omega)}{2}}$$

in Eq. 64. To account for this phase term, the operator A can be written as $$A(r, \omega) = \frac{\left(G(r, \omega)e^{\frac{i\phi(\omega)}{2}}\right)^H U_{sig}(\omega)V_{sig}^H(\omega)\left(G(r, \omega)e^{\frac{i\phi(\omega)}{2}}\right)^*}{\|G(r, \omega)\|^2}$$ Eq. 68

$$= e^{-i\phi(\omega)} \frac{G^H(r, \omega)U_{sig}(\omega)V_{sig}^H(\omega)G^*(r, \omega)}{\|G(r, \omega)\|^2}.$$

Eq. 68 demonstrates the importance of including the phase response $\varphi(\omega)$ in the calculation of the operator A. Numerical and experimental studies provided below show that the PC-MUSIC imaging algorithm 200 with compensation for phase response yields accurate target localization and significantly higher resolution than the original PC-MUSIC and TR-MUSIC algorithms.

FIG. 13 illustrates a PC-MUSIC imaging algorithm 200 that compensates for phase response in accordance with the present invention. As shown in FIG. 13, the phase response of the transducers, which is generated at step 206, is used to generate the inter-element transfer matrix at step 208. The phase response 206 combines the electro-mechanical response 202 and transmitted-pulse phase response 204. Next, time reversal matrix 210 is generated. Finally, the pseudo-spectrum with phase response is generated in step 212 using the phase response-adjusted operator A of Eq. 68 as a function of the pseudo spectrum Eq. 65.

The phase response $\varphi(\omega)$ must be known prior to calculating the phase-coherent pseudo-spectrum. In the following, we describe an experimental method for measuring this response.

The phase response $\varphi(\omega)$ must be known prior to calculating the phase-coherent pseudo-spectrum in step 212. FIG. 14A details an experimental method 250 for measuring the phase response of a given transducer array 14.

When a single point scatterer is scanned with an ultrasound transducer array 14 under noiseless conditions, the rank of the matrix K is equal to one. In that case, the left and right singular vectors $u_1$ and $v_1$, are written as:

$$u_1(\omega) = \frac{G(r_1, \omega)}{\|G(r_1, \omega)\|} e^{i\left(\theta_1 + \frac{i\phi(\omega)}{2}\right)},$$ Eq. 69

$$v_1(\omega) = \frac{G^*(r_1, \omega)}{\|G(r_1, \omega)\|} e^{i\left(\theta_1 - \frac{i\phi(\omega)}{2}\right)}.$$

The phase response of transducer elements is estimated by first scanning a phantom containing a homogeneous background medium and a glass micro-sphere at a known location, as specified in step 252.

FIG. 14B shows scanning step 252 in greater detail. First, a glass microsphere is positioned a specified distance from element I at step 270. Next, element (i) transmits and receives an echo from the target at step 272. At step 274, the algorithm queries whether element i=N. If not (step 278), the algorithm moves to the next transducer element (i+1), and repeats step 270. If yes, at step 276 all elements 16 in the array 14 are scanned, the acquisition is ended, and the N measured backscattered signals are averaged (to reduce noise effects) before SVD analysis and calculation of the Green's vector at step 254 (FIG. 14A).

For accurate calculation of the Green's vector, the sound speed of the phantom 258 must be known, in addition to the sphere location 256 and geometry 260 of the transducers 16. If the scatterer location 256, the geometry of transducer elements 260, and the sound speed of the background medium 258 are known, the Green's vector to the point scatterer $G(r_1,\omega)$ can be calculated at step 254. By calculating the Eq. 70 at each frequency $\omega$:

$$\frac{G^H(r_1, \omega)u_1(\omega)v_1^H(\omega)G^*(r_1, \omega)}{\|G(r_1, \omega)\|^2} = e^{i\varphi(\omega)},$$ Eq. 70 the phase factor $e^{i\varphi(\omega)}$ can be obtained at step 280.

The glass micro-sphere must be much smaller than the ultrasound wavelength to be considered as a point scatterer. The phase response can be estimated by calculating Eq. 70 over the bandwidth of the transducer array. In the presence of noise, Eq. 70 does not yield a phase factor with a unit amplitude. In that case, the phase angle is first obtained at step 282 by calculating the phase of the left-hand side. Note that if the location of the glass micro-sphere is not known beforehand, it can be obtained using classic TR-MUSIC. Since classic TR-MUSIC does not use phase information, the pseudo-spectrum peaks at the exact location of the glass micro-sphere.

Numerical simulations were performed to demonstrate the improvement in the resolution and accuracy of target localization when accounting for the phase response of transducer elements in the PC-MUSIC algorithm 200 of the present invention. Images of point scatterers obtained with PC-MUSIC and TR-MUSIC were compared.

A linear ultrasound transducer array 14 was simulated in which each element 16 was excited sequentially and the scattered signals are measured by all elements of the array 14 (see FIG. 3). Ultrasound signals scattered from point scatterers that are distributed in a homogeneous medium with an ultrasound attenuation coefficient of 0.5 dB/cm-MHz and a sound speed of 1540 m/s were obtained. The array 14 comprised of 128 elements with a pitch of 325 µm. The face of each element 16 was 300 µm by 6 mm. The resonant frequency of each element was 7.5 MHz and the 6-dB fractional bandwidth was 65%.

The Foldy-Lax model was used to calculate the ultrasound scattered signals. Given the sound speed of the medium and the complex wavenumber $\underline{k}$, the double integrals of Eq. 61 were numerically evaluated over the surfaces of the transducer elements. The transfer function $F(\omega)$ was obtained by performing FFT on a Gaussian-modulated sinusoidal pulse with a center frequency of 7.5 MHz and a 6 dB fractional bandwidth. Time zero of the Gaussian-modulated sinusoidal pulse corresponds to the time where the leading pulse envelope falls to 60 dB. The time-dependent signals are calculated using the inverse FFT of the spectra obtained with the Foldy-Lax model.

To compare classic TR-MUSIC versus PC-MUSIC, scattering from a single point scatterer was simulated. The scatterer was located 2 cm axially from the center of the transducer array 14. Uncorrelated and zero-mean Gaussian noise was added to the recorded time signals with an SNR of 10 dB. The SNR is defined as $$SNR = 20\log_{10}\left(\frac{S^2}{2\sigma^2}\right),$$ Eq. 71 where $\sigma^2$ is the variance of the Gaussian noise, and S is the maximum amplitude of the weakest recorded signal.

FIG. 15A through FIG. 15C show images of the point scatterer obtained with TR-MUSIC (FIG. 15A), PC-MUSIC without phase-response compensation (FIG. 15B) and with phase-response compensation (FIG. 15C). The images are formed by calculating the logarithm of the normalized pseudospectra, and displaying them with a 40 dB dynamic range. The image obtained with TR-MUSIC peaks at the true scatterer location, but suffers from an elongation artifact. The extent of this artifact depends on the SNR and the point-spread function of the transducer array 14 at the location of the scatterer. When the phase response of the transducer elements 16 is ignored, as done previously in the art, the image obtained with PC-MUSIC peaks at the wrong location. When the phase response is compensated, the pseudo-spectrum peaks at the true scatterer location, and the size of the bright region in the image is smaller than those of images FIG. 15A and FIG. 15B. The images obtained with the original PC-MUSIC appear to have a ringing artifact in the axial direction. This artifact is caused by a decrease in the amplitude of the operator A and a change in its phase away from the scatterer location.

To understand why the original PC-MUSIC peaks at the wrong location when the phase response is not accounted for, the amplitude and the phase of the operators A for TR-MUSIC, and for PC-MUSIC (without phase compensation) were calculated. The operators were calculated at the true scatterer location, and at the peak of the pseudo-spectrum in FIG. 15B.

The amplitudes of the operator A were found to be larger at the true scatterer location than those at the peak of the pseudo-spectrum, but were nearly identical for TR-MUSIC and PC-MUSIC. Since noise is added to the scattered signals in the time domain, the SNR changes with frequency according to the response of the transducers. As a consequence, the amplitude of A at the scatterer location has a maximum at the resonant frequency. Note that in the absence of noise, the amplitude of A at the scatterer location should be equal to one at all frequencies.

In the frequency range of 4-11 MHz, it was found that the phase of the operator A for PC-MUSIC is almost equal (except for slight fluctuations caused by noise) to the phase response of the transducer elements used in the numerical simulation. Outside this frequency range, noise starts to dominate. At the scatterer location, the amplitude of A is nearly constant and the phase spans approximately $4\pi$. Therefore, the sum $$\sum_{\Delta\omega} A(r, \omega)$$

is approximately zero, resulting in a small value for the pseudo-spectrum, and consequently, no peak exists at the true scatterer location. At the peak of the pseudo-spectrum, the phase of A changes very slowly with frequency, so the sum $$\sum_{\Delta\omega} A(r, \omega)$$

is much larger, leading to a peak of the pseudo-spectrum at the wrong scatterer location.

To explore the resolution limits achieved with the MUSIC algorithms, the amplitude and the phase of the operators A for was plotted for the TR-MUSIC algorithm and PC-MUSIC algorithm 200 with phase compensation at different test points away from the point scatterer. The plots are shown in FIG. 16A through FIG. 16H.

The amplitude of the operator A decreases with increasing separation from the scatter location. In the frequency range of 4-11 MHz, the phase of the operator A is close to zero at the scatterer location because the phase response of the transducer elements is accurately compensated. At the test points that are located $\lambda/4$, $\lambda/2$, and $\lambda$ below the scatterer location, the phase of the operator A spans approximately $\pi$, $2\pi$, and $4\pi$ radians, respectively.

The size of the image of a point scatterer can be used as a measure of the spatial resolution. We take the spatial resolution as the shortest axial distance from the scatterer to the point of maximum destructive interference, i.e. the point where the sum $$\sum_{\Delta\omega} A(r, \omega)$$

is close to zero. The shortest distance in the axial direction was chosen, because the axial resolution is much lower than the lateral resolution. In our numerical example, the pseudo-spectrum falls nearly to zero at a location $\lambda/2$ below the scatterer location.

Figure 16A:
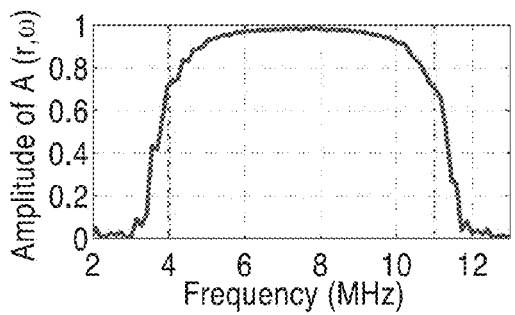
Figure 16B:
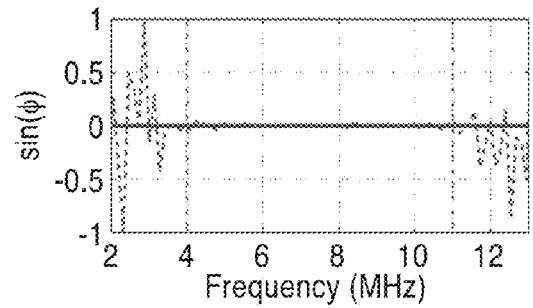
Figure 16C:
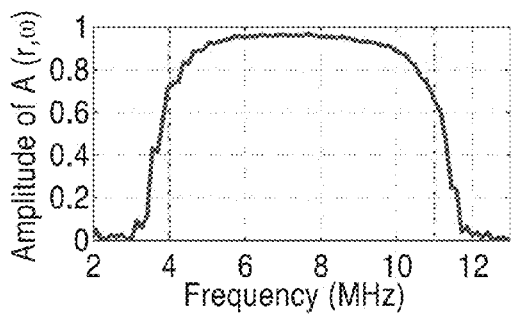
Figure 16D:
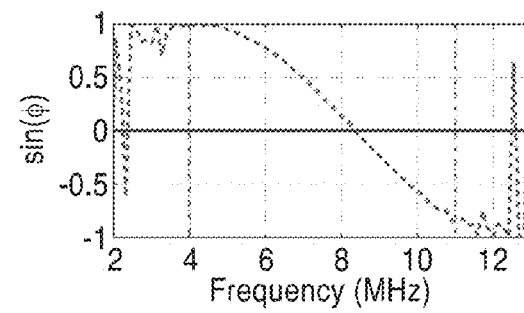
Figure 16E:
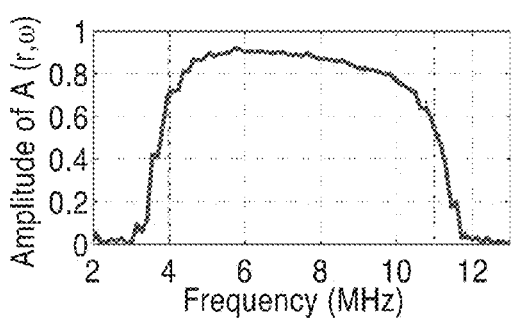
Figure 16F:
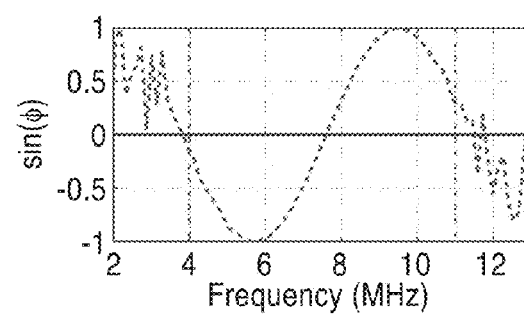
Figure 16G:
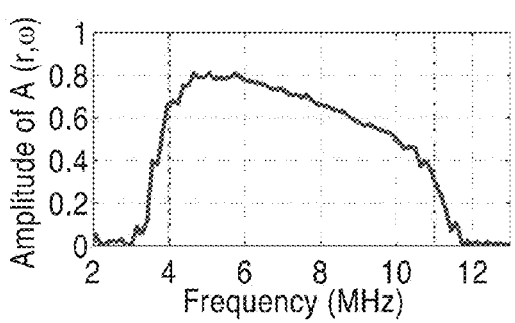
Figure 16H:
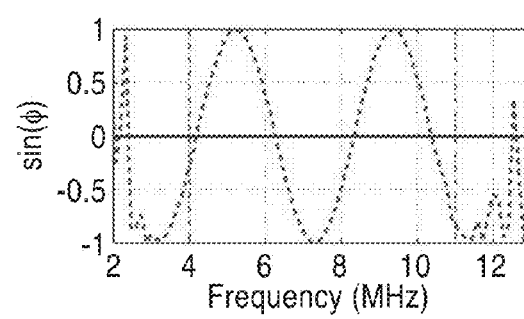
Figure 18A:
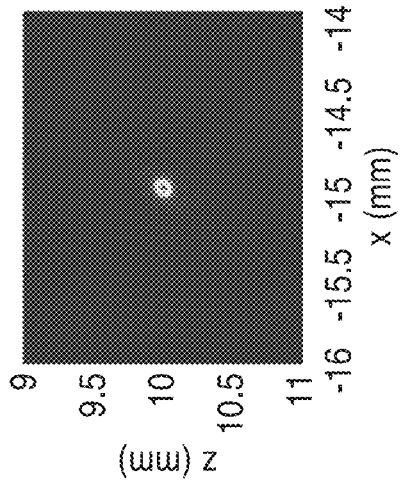
Figure 18B:
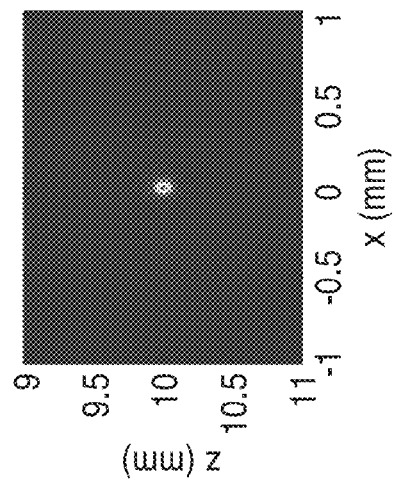
Figure 18C:
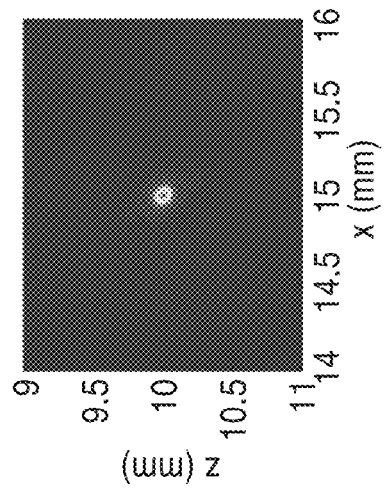
Figure 18D:
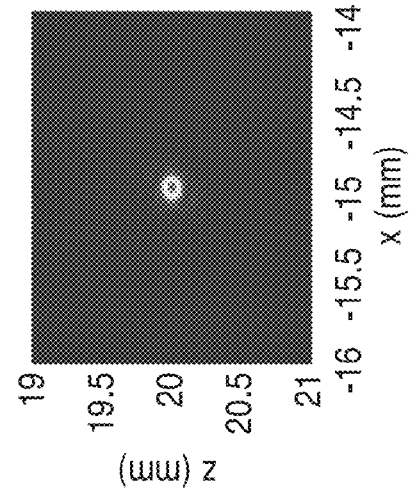
Figure 18E:
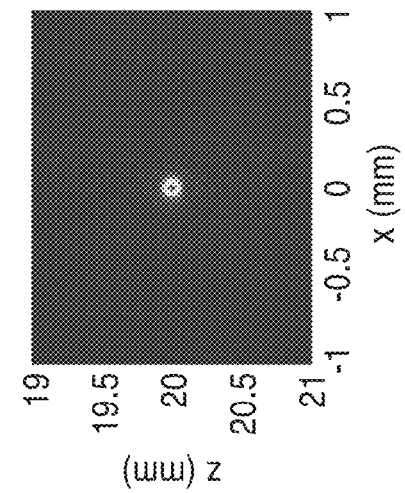
Figure 18F:
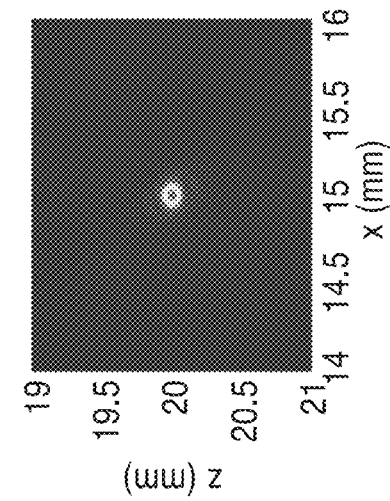

As shown in FIG. 16F, the phase of A at this point spans nearly $2\pi$ in the 4-11 MHz frequency range, resulting in a value of $$\sum_{\Delta\omega} A(r,\omega)$$

that is close to zero. At distances larger than $\lambda/2$ from the scatterer, the phase of A spans angles larger than $2\pi$. The pseudo-spectrum will be close to zero at the spatial locations where the phase of A spans multiples of $2\pi$. This explains the ringing artifact away from the scatterer location.

If the noise is significantly lower, the usable frequency range should increase slightly. Then, over the increased range, the phase of A spans $2\pi$ at a location smaller than $\lambda/2$, yielding a higher spatial resolution. The usable frequency range is determined mainly by the transducer bandwidth and to a smaller extent by the SNR.

To study the point-spread functions of TR-MUSIC and PC-MUSIC with phase response compensation, we construct images of a single scatterer placed at different positions away from the center of the transducer array. The SNR is 10 dB. FIG. 17A through FIG. 17F and FIG. 18A through FIG. 18F show the images obtained with TR-MUSIC and PC-MUSIC with phase response compensation, respectively. The images are constructed using frequencies within 4-11 MHz, and displayed with a 40 dB dynamic range. The size of the bright regions indicates that PC-MUSIC with phase response compensation gives significantly higher resolution than TR-MUSIC. In both algorithms, the resolution is higher near the face of the array. When the scatterer is positioned lateral to the center axis of the array, the images are tilted toward the center of the array. These characteristics are governed by the geometry of the transducer array 14.

Phantom experiments were conducted using a custom-built, real-time synthetic-aperture ultrasound (SAUS) imaging system 10 and a linear transducer array 14. The array 14 comprised 128 elements 16 with a pitch of 325 μm. The face of each element 16 is 300 μm by 6 mm. The resonant frequency of each element is approximately 7.5 MHz and the 6 dB fractional bandwidth of approximately 65%. The ultrasound system gives access to the 128×128 measured radio frequency (RF) signals.

The method 250 shown in FIG. 14A and FIG. 14B was used to estimate the phase response of the transducer elements 16. A phantom was scanned with a homogeneous background medium and a glass micro-sphere. The sound speed of the phantom was 1500 ms$^{-1}$ and the diameter of the micro-sphere was approximately 250 μm. The operator A was calculated with Eq. 70 at the location of the micro-sphere. The double integrals in the equation for the Green's vector $G(r_m,\omega)$ were numerically evaluated over the surfaces of the transducer elements 16. Since the sound speed of the phantom is well known, we choose the location of the micro-sphere as the position where the TR-MUSIC pseudo-spectrum is maximum.

The amplitude and the phase of the operator A for PC-MUSIC with phase response compensation were obtained at the usable frequency range between 2.5 and 11 MHz. In this range, the measured phase response of the transducer elements was found. The amplitude of the operator A is close to 1 at lower frequencies, but decreases slightly at higher frequencies. That is because at high frequencies, the glass micro-sphere can no longer be considered as a point scatterer and Eq. 70 is not exact.

Images of the glass micro-sphere were obtained using TR-MUSIC and PC-MUSIC with and without phase response compensation. While the TR-MUSIC accurately located the sphere, it still suffered from an elongation artifact. When the phase response is ignored, PC-MUSIC peaks at a wrong location. However, the sphere is accurately located when the phase response is accounted for. As with the numerical studies above, ringing artifacts are observed in the PC-MUSIC image without phase response compensation.

The MUSIC algorithms were also tested on two tissue-mimicking phantoms. Phantom 1 had a homogeneous background and contained a number of glass micro-spheres distributed inside a plane. The diameters of the micro-spheres are approximately 250 μm. Phantom 2 had an inhomogeneous background medium (ATS laboratories Inc., ATS551) and contains monofilament line targets with a diameter of 50 μm. The phantoms were scanned with the SAUS system 10. Images were constructed of the phantoms using TR-MUSIC and PC-MUSIC, and compared to the synthetic-aperture images generated with the SAUS system. Phantom 1 was also radio-graphed using X-ray mammography and the image was compared to the MUSIC and SAUS images.

The time-windowing methods 50 and 100 of the present invention shown in FIG. 5 and FIG. 6 were used to construct the MUSIC images. In this method, the imaging plane was divided into 2 mm×2 mm squares, where each sub-region was images separately. The MUSIC calculations were performed on the windowed backscattered signals originating from the chosen sub-region. This method improves image quality when the rank of inter-element response matrix is large. To accurately image the scatterers located at the edges of the sub-regions and to avoid edge artifacts, images of sub-regions that are overlapped one another by 50% were obtained. The entire image was then formed by combining the images of all overlapped sub-regions using a bi-linear interpolation weighting scheme. To simplify the calculation of the pseudo-spectra, the number of signal singular vectors was fixed at 5. For PC-MUSIC with phase response compensation, the operator A corresponding to Eq. 68 was calculated using the phase response measured with the glass micro-sphere via method 250.

FIG. 19A through FIG. 19D show images for Phantom 1 obtained with different modalities. All the images are displayed with a 40 dB dynamic range. FIG. 19A shows the X-ray mammography image, which is inverted for better comparison with the ultrasound images. The corresponding SAUS image is shown in FIG. 19B. It is clear that the SAUS image of FIG. 19B has lower resolution compared to the X-ray mammography image of FIG. 19A. In the SAUS image, the glass spheres appear larger than their actual sizes, and some closely-separated spheres appear as one. Although the glass spheres are the only inhomogeneities in the phantom, speckle noise is observed in the SAUS image. The speckle noise is possibly caused by multiple scattering among the glass spheres.

Image noise is significantly reduced in the MUSIC images (FIGS. 19C and 19D). Compared to the SAUS image of FIG. 19B, the TR-MUSIC image of FIG. 19C has a higher lateral resolution. However, the elongation artifact significantly reduces the axial resolution, leading to several spheres that are separated axially appearing as one. In the PC-MUSIC image with phase response compensation, all the spheres are accurately detected. The spatial resolution of the PC-MUSIC image with phase response compensation is significantly higher MUSIC than that achieved with TR-MUSIC and SAUS.

CONCLUSION

A generalized TR-MUSIC algorithm was developed to account for the attenuation in the medium and the finite-size effects of the transducer elements. It was demonstrated that that the generalized algorithm yields higher resolution images compared to those obtained without accounting for attenuation or diffraction effects. Without noise in the recorded RF signals, the algorithm yields super-resolution. When noise corrupts the recorded signals, the image resolution decreases. The axial resolution degrades more than the lateral resolution because of the spatial extent of the coherent point spread function. A windowed TR-MUSIC algorithm was also developed for imaging point scatterers when their number exceeds the number of transducer elements. This method is based on dividing the imaging plane into sub-regions and applying the TR-MUSIC algorithm to the windowed backscattered signals corresponding to each sub-region. The images of all sub-regions are then combined to form the total image.

It was shown that to optimize results, the sub-region size and the number of eigenvectors used to calculate the pseudo-spectrum can be chosed accordingly. The sub-region size is preferably small enough such that that the number of scatterers within is much smaller than the number of transducer elements, so that the effects of the nuisance signals from outside the sub-region are negligible. The number of eigenvectors is preferably chosen such that the corresponding eigenvalues are close to zero. It was demonstrated through a phantom experiment that the windowed TR-MUSIC algorithm yields a significantly higher image quality compared to the original TR-MUSIC algorithm. It was also shown that the lateral resolution obtained using the windowed TR-MUSIC algorithm is far superior to the lateral resolution of the image obtained using synthetic-aperture imaging.

The windowed TR-MUSIC algorithm of the present invention is ideally suited for detection of breast microcalcifications.

A modified TR-MUSIC imaging algorithm was also developed to account for the ultrasound scattering from the density contrast, as well as the compressibility contrast. It was demonstrated that the modified TR-MUSIC imaging algorithm of the present invention yields higher-resolution images compared to those obtained with the original TR-MUSIC algorithm in which the density contrast is ignored. Without noise in the recorded RF signals, the modified TR-MUSIC imaging algorithm of the present invention yields super-resolution. The image resolution decreases when noise corrupts the recorded signals.

An inversion method was also developed for estimating the compressibility and density contrasts of small, point-like scatterers embedded in a medium. In this method, the target locations and the electro-mechanical response of the transducer array are preferably known in advance. The target locations can be estimated using the modified TR-MUSIC imaging algorithm of the present invention, while the electromechanical response can be estimated using calibration methods. The estimates of the compressibility and density contrasts are scaled by the electromechanical response when the latter is not known.

It was shown that the relative errors in the estimates of the compressibility and density contrasts decrease with increasing the signal-to-noise ratio. It was also found that for a given signal-to-noise ratio, the relative error in the density contrast is much higher than that of the compressibility contrast when the ratio of the density contrast to the compressibility contrast is small, and vice versa.

It was further demonstrated that the modified TR-MUSIC imaging algorithm of the present invention yields super-resolution images with accurate target localization when the imaged medium contains numerous targets with varying density and compressibility contrasts. The super-resolution capability of the new TR-MUSIC algorithm is particularly beneficial for applications in medical ultrasound imaging. One particular area of interest is the detection and quantification of breast micro-calcifications, which are the first sign of breast cancer for numerous breast cancer cases.

The phase-coherent MUSIC (PC-MUSIC) algorithm was modified to account for the phase response of transducer elements. In addition, an experimental method was developed to estimate the phase response using scattered signals from a glass micro-sphere embedded in a homogeneous background medium. It was demonstrated through numerical and experimental studies that the modified PC-MUSIC algorithm with phase response compensation improves target localization and image resolution, compared to the original PC-MUSIC algorithm that ignores the phase response of transducer elements.

From the description herein it will be appreciated that the invention can be embodied in various ways which include, but are not limited to, the following:

1. A method of performing ultrasound imaging of a medium, the method comprising: exciting a first transducer element in an array of transducer elements to direct an ultrasound signal into a target region of the medium; receiving a backscatter signal from the target region within the medium with the array of transducer elements; generating an inter-element transfer matrix of the received backscatter signal; said inter-element transfer matrix comprising density contrast data relating to one or more scatterers within said medium; generating a generalized time-reversal (TR) matrix from the inter-element transfer matrix; and generating a pseudo-spectrum for generalized TR-Music imaging of the target region; said pseudo-spectrum comprising density contrast data relating to one or more scatterers within said medium.

2. A method as recited in any of the preceding embodiments: wherein said inter-element transfer matrix further comprises compressibility contrast data; and wherein said pseudo-spectrum comprises density contrast data and compressibility contrast data relating to one or more scatterers within said medium.

3. A method as recited in any of the preceding embodiments, further comprising obtaining said density contrast data and compressibility contrast data from least squares estimation of a pseudo-spectrum generated from TR-MUSIC imaging.

4. A method as recited in any of the preceding embodiments, wherein said step of generating an inter-element transfer matrix comprises calculating the inter-element transfer matrix as a function of the electro-mechanical response of each transducer element in the array.

5. A method as recited in any of the preceding embodiments, wherein said step of generating an inter-element transfer matrix comprises calculating the inter-element transfer matrix as a function of the diffraction response of each transducer element in the array.

6. A method as recited in any of the preceding embodiments, wherein said step of generating an inter-element transfer matrix comprises calculating the inter-element transfer matrix as a function of the attenuation in the target region.

7. A method as recited in any of the preceding embodiments, wherein diffraction response of each transducer element is a function of finite size effects of the array of transducer elements.

8. A method as recited in any of the preceding embodiments, wherein said inter-element transfer matrix K is calculated according to the function:

$$K = F(\omega)\sum_{m=1}^{M}\gamma_\kappa(r_m)A(r_m)A^T(r_m) + \gamma_\rho(r_m)[\ B_1(r_m)\ \ B_2(r_m)\ \ ...\ \ B_N(r_m)\ ]$$

where $r_m$ is a location of an $m^{th}$ point scatter, $\gamma_\rho$ is the density contrast, $\gamma_\kappa$ is the compressibility contrast, and superscript T denotes the transpose of the vector, $B_n(r_m)$ is a vector given by: $A^T(r_m)=[a_1(r_m)\ a_2(r_m)\ ...\ a_N(r_m)]$, and $A(r_m)$ is a vector given by:

$$B_n^T(r_m)=[\cos(\theta_{m_1,n})a_1(r_m)a_n(r_m)\cos(\theta_{m_2,n})a_2(r_m)a_n(r_m)\ ...\ \cos(\theta_{m_N,n})a_N(r_m)a_n(r_m)].$$

9. A method as recited in any of the preceding embodiments, wherein the pseudo-spectrum is calculated according to the equation:

$$\Phi(r) = \frac{1}{\sum_{\sigma_p=0}|u_p^\dagger A(r)|^2} + \frac{1}{\sum_{\sigma_p=0}\sum_{n=1}^{N}|u_p^\dagger B_n(r)|^2}$$

where superscript † denotes the transpose of the complex conjugate of a vector or a matrix, $\sigma_p$ are singular values, and $u_p$ is a left singular vector $v_p$ and is a right singular vector.

10. A method as recited in any of the preceding embodiments, wherein the step of receiving backscatter signal comprises: dividing an imaging plane of the target region into a plurality of sub-regions; imaging each sub-region in the plurality of sub-regions separately; and combining each sub-region to form an entire image of the target region.

11. A method as recited in any of the preceding embodiments, wherein sub-region size is chosen such that the number of scatterers within the sub-region is smaller than the number of transducer elements in the array.

12. A method as recited in any of the preceding embodiments, wherein spatial locations in each sub-region correspond with windowed time samples within the imaging plane.

13. A method as recited in any of the preceding embodiments, wherein the medium comprises a tissue region within the body of a patient.

14. An ultrasound imaging system for imaging of a medium, the system comprising: (a) a processor; and (b) programming executable on said processor for: (i) exciting a first transducer element in an array of transducer elements to direct an ultrasound signal into a target region of the medium; (ii) receiving a backscatter signal from the target region within the medium with the array of transducer elements; (iii) generating an inter-element transfer matrix of the received backscatter signal; (iv) said inter-element transfer matrix comprising density contrast data relating to one or more scatterers within said medium; (v) generating a generalized time-reversal (TR) matrix from the inter-element transfer matrix; and (vi) generating a pseudo-spectrum for generalized TR-Music imaging of the target region; (vii) said pseudo-spectrum comprising density contrast data relating to one or more scatterers within said medium.

15. A system as recited in any of the preceding embodiments: wherein said inter-element transfer matrix further comprises compressibility contrast data; and wherein said pseudo-spectrum comprises density contrast data and compressibility contrast data relating to one or more scatterers within said medium.

16. A system as recited in any of the preceding embodiments, wherein the density contrast data and compressibility contrast data are obtained from least squares estimation of a pseudo-spectrum generated from TR-MUSIC imaging.

17. A system as recited in any of the preceding embodiments, wherein said step of generating an inter-element transfer matrix comprises calculating the inter-element transfer matrix as a function of the electro-mechanical response of each transducer element in the array.

18. A system as recited in any of the preceding embodiments, wherein said step of generating an inter-element transfer matrix comprises calculating the inter-element transfer matrix as a function of the diffraction response of each transducer element in the array.

19. A system as recited in any of the preceding embodiments, wherein said step of generating an inter-element transfer matrix comprises calculating the inter-element transfer matrix as a function of the attenuation in the target region.

20. A system as recited in any of the preceding embodiments, wherein diffraction response of each transducer element is a function of the finite size effects of the array of transducer elements.

21. A system as recited in any of the preceding embodiments, wherein said inter-element transfer matrix K is calculated according to the function:

$$K = F(\omega)\sum_{m=1}^{M}\gamma_\kappa(r_m)A(r_m)A^T(r_m) + \gamma_\rho(r_m)[\ B_1(r_m)\ \ B_2(r_m)\ \ ...\ \ B_N(r_m)\ ]$$

where $r_m$ is a location of an $m^{th}$ point scatter, $\gamma_\rho$ is the density contrast, $\gamma_\kappa$ is the compressibility contrast, and superscript T denotes the transpose of the vector, where $B_n(r_m)$ is a vector given by:

$$A^T(r_m)=[a_1(r_m)a_2(r_m)\ ...\ a_N(r_m)],$$

and where $A(r_m)$ is a vector given by:

$$B_n^T(r_m)=[\cos(\theta_{m_1,n})a_1(r_m)a_n(r_m)\cos(\theta_{m_2,n})a_2(r_m)a_n(r_m)\ ...\ \cos(\theta_{m_N,n})a_N(r_m)a_n(r_m)].$$

22. A system as recited in any of the preceding embodiments, wherein the pseudo-spectrum is calculated according to the equation:

$$\Phi(r) = \frac{1}{\sum_{\sigma_p=0}|u_p^\dagger A(r)|^2} + \frac{1}{\sum_{\sigma_p=0}\sum_{n=1}^{N}|u_p^\dagger B_n(r)|^2}$$

wherein superscript † denotes the transpose of the complex conjugate of a vector or a matrix, $\sigma_p$ are singular values, and $u_p$ is a left singular vector $v_p$ and is a right singular vector.

23. A system as recited in any of the preceding embodiments, wherein the step of receiving the backscatter signal comprises: dividing an imaging plane of the target region into a plurality of sub-regions; imaging each sub-region in the plurality of sub-regions separately; and combining each sub-region to form an entire image of the target region.

24. A system as recited in any of the preceding embodiments, wherein sub-region size is chosen such that the number of scatterers within the sub-region is smaller than the number of transducer elements in the array.

25. A system as recited in any of the preceding embodiments, wherein spatial locations in each sub-region correspond with windowed time samples within the imaging plane.

26. A method as recited in any of the preceding embodiments, wherein the medium comprises a tissue region within the body of a patient.

27. A method of performing ultrasound imaging of a medium, the method comprising: exciting a first transducer element in an array of transducer elements to direct an ultrasound signal into a target region of the medium; receiving a backscatter signal from the target region within the medium with the array of transducer elements; generating an inter-element transfer matrix of the received backscatter signal; said inter-element transfer matrix comprising data relating to a phase response of the array of transducer elements; generating a pseudo-spectrum for phase coherent (PC) Music imaging of the target region; wherein said pseudo-spectrum is compensated for the phase response of the array of transducer elements.

28. A method as recited in any of the preceding embodiments, further comprising: estimating the phase response of the array of transducer elements; and wherein said inter-element transfer matrix is generated as a function of the estimated phase response of the array of transducer elements.

29. A method as recited in any of the preceding embodiments, wherein said step of estimating the phase response of the array of transducer elements comprises scanning a phantom containing a homogenous background medium and a point scatterer.

30. A method as recited in any of the preceding embodiments, wherein said point scatterer comprises a microsphere positioned at a known location from the array of transducer elements.

31. A method as recited in any of the preceding embodiments, wherein said step of scanning a phantom comprises measuring backscatter signals from said point scatterer, the method further comprising: generating an inter-element response matrix at several frequencies in the bandwidth of the array of transducer elements; calculating singular value decomposition of the inter-element response at the several frequencies; and estimating phase response of the array of transducer elements.

32. A method as recited in any of the preceding embodiments, wherein said step of estimating phase response comprises calculating the Green's vector to the point scatterer.

33. A method as recited in any of the preceding embodiments, wherein said step of estimating phase response comprises obtaining a phase factor $$e^{\frac{i\phi(\omega)}{2}}$$

at each frequency $\omega$ according to the equation:

$$\frac{G^H(r_1,\omega)u_1(\omega)v_1^H(\omega)G^*(r_1,\omega)}{\|G(r_1,\omega)\|^2} = e^{i\phi(\omega)}.$$

where $G(r_1,\omega)$ $u_1$ is the Green's vector to the point scatterer, and $u_1$ and $v_1$ are left and right singular vectors.

34. A method as recited in any of the preceding embodiments, wherein said measured backscattered signals are averaged prior to calculating singular value decomposition.

35. A method as recited in any of the preceding embodiments, wherein said pseudo-spectrum is calculated according to:

$$P(r,\omega) = \frac{1}{1 - \sum_{\Delta\omega} A(r,\omega)}$$

where $$A(r,\omega) = \frac{\left(G(r,\omega)e^{\frac{i\phi(\omega)}{2}}\right)^H U_{sig}(\omega)V_{sig}^H(\omega)\left(G(r,\omega)e^{\frac{i\phi(\omega)}{2}}\right)^*}{\|G(r,\omega)\|^2}$$

$$= e^{-i\phi(\omega)}\frac{G^H(r,\omega)U_{sig}(\omega)V_{sig}^H(\omega)G^*(r,\omega)}{\|G(r,\omega)\|^2}.$$

36. A method as recited in any of the preceding embodiments, wherein said step of receiving a backscatter signal further comprises: dividing an imaging plane of the target region into a plurality of sub-regions; imaging each sub-region in the plurality of sub-regions separately; and combining each sub-region to form an entire image of the target region.

37. An ultrasound imaging system for imaging of a medium, the system comprising: (a) a processor; and (b) programming executable on said processor for: (i) exciting a first transducer element in an array of transducer elements to direct an ultrasound signal into a target region of the medium; (ii) receiving a backscatter signal from the target region within the medium with the array of transducer elements; (iii) generating an inter-element transfer matrix of the received backscatter signal; (iv) said inter-element transfer matrix comprising data relating to a phase response of the array of transducer elements; (v) generating a pseudo-spectrum for phase coherent (PC) Music imaging of the target region; (vi) wherein said pseudo-spectrum is compensated for phase response of the array of transducer elements.

38. A system as recited in any of the preceding embodiments, wherein said programming further performs steps comprising: estimating phase response of the array of transducer elements; and wherein inter-element transfer matrix is generated as a function of the estimated phase response of the array of transducer elements.

39. A system as recited in any of the preceding embodiments, wherein said step of estimating phase response of the array of transducer elements comprises scanning a phantom containing a homogenous background medium and a point scatterer.

40. A system as recited in any of the preceding embodiments, wherein said point scatterer comprises a microsphere positioned at a known location from the array of transducer elements.

41. A system as recited in any of the preceding embodiments, wherein said step of scanning a phantom comprises measuring backscatter signals from the point scatterer, the method further comprising: generating an inter-element response matrix at several frequencies in the bandwidth of the array of transducer elements; calculating singular value decomposition of the inter-element response at the several frequencies; and estimating the phase response phase response of the array of transducer elements.

42. A system as recited in any of the preceding embodiments, wherein said step of estimating phase response comprises calculating the Green's vector to the point scatterer.

43. A system as recited in any of the preceding embodiments, wherein said step of estimating phase response further comprises obtaining a phase factor $$e^{\frac{i\phi(\omega)}{2}}$$

at each frequency ω according to the equation:

$$\frac{G^H(r_1, \omega)u_1(\omega)v_1^H(\omega)G^*(r_1, \omega)}{\|G(r_1, \omega)\|^2} = e^{i\phi(\omega)}.$$

where $G(r_1,\omega)$ $u_1$ is the Green's vector to the point scatterer, and $u_1$ and $v_1$ are left and right singular vectors.

44. A system as recited in any of the preceding embodiments, wherein said measured backscattered signals are averaged prior to calculating singular value decomposition.

45. A system as recited in any of the preceding embodiments, wherein said pseudo-spectrum is calculated according to:

$$P(r, \omega) = \frac{1}{1 - \sum_{\Delta\omega} A(r, \omega)}$$

where $$A(r, \omega) = \frac{\left(G(r, \omega)e^{\frac{i\phi(\omega)}{2}}\right)^H U_{sig}(\omega)V_{sig}^H(\omega)\left(G(r, \omega)e^{\frac{i\phi(\omega)}{2}}\right)^*}{\|G(r, \omega)\|^2}$$
$$= e^{-i\phi(\omega)} \frac{G^H(r, \omega)U_{sig}(\omega)V_{sig}^H(\omega)G^*(r, \omega)}{\|G(r, \omega)\|^2}.$$

46. A system as recited in any of the preceding embodiments, wherein said step of receiving a backscatter signal further comprises: dividing an imaging plane of the target region into a plurality of sub-regions; imaging each sub-region in the plurality of sub-regions separately; and combining each sub-region to form an entire image of the target region.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula (e), or computational depiction(s).

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

True, estimated, and relative errors in $\gamma_\kappa$ and $\gamma_\rho$ for five point targets

| Point Targets | True $\gamma_\kappa$ | True $\gamma_\rho$ | Estimated $\gamma_\kappa$ | Estimated $\gamma_\rho$ | |RE $\gamma_\kappa$| (%) | |RE $\gamma_\rho$| (%) |
|---|---|---|---|---|---|---|
| 1 | 0.0273 | 0.0448 | 0.0275 | 0.0451 | 0.6895 | 0.62 |
| 2 | 0.0325 | 0.005 | 0.0338 | 0.0015 | 4.0139 | 30.66 |
| 3 | 0.005 | 0.0332 | 0.0068 | 0.033 | 36 | 0.578 |
| 4 | 0.0306 | 0.0154 | 0.0312 | 0.0159 | 1.95 | 3.3595 |
| 5 | 0.0158 | 0.0256 | 0.016 | 0.0258 | 1.425 | 0.393 |

What is claimed is:

1. A method of performing ultrasound imaging of a medium, the method comprising:

exciting a first transducer element in an array of transducer elements to direct an ultrasound signal into a target region of the medium;

receiving a backscatter signal from the target region within the medium from the array of transducer elements;

generating an inter-element transfer matrix of the received backscatter signal;

said inter-element transfer matrix comprising density contrast data relating to one or more scatterers within said medium;

generating a generalized time-reversal (TR) matrix from the inter-element transfer matrix; and generating a pseudo-spectrum for generalized TR-Music imaging of the target region, said pseudo-spectrum comprising density contrast data relating to one or more scatterers within said medium, wherein generating the inter-element transfer matrix comprises calculating the inter-element transfer matrix as a function of an electro-mechanical response of each transducer element in the array, a diffraction response of each transducer element in the array, and attenuation in the target region.

2. A method as recited in claim 1:

wherein said inter-element transfer matrix further comprises compressibility contrast data; and wherein said pseudo-spectrum comprises density contrast data and compressibility contrast data relating to one or more scatterers within said medium.

3. A method as recited in claim 2, further comprising obtaining said density contrast data and compressibility contrast data from least squares estimation of a pseudo-spectrum generated from TR-MUSIC imaging.

4. A method as recited in claim 2, wherein said inter-element transfer matrix K is calculated according to the function:

$$K = F(\omega)\sum_{m=1}^{M} \gamma_\kappa(r_m)A(r_m)A^T(r_m) + \gamma_\rho(r_m)[\begin{array}{cccc} B_1(r_m) & B_2(r_m) & \ldots & B_N(r_m) \end{array}]$$

where $F(\omega)$ is a electromechanical transfer function, M is the number of the scatterers within said medium, $r_m$ is a location of an $m^{th}$ point scatter, $\gamma_\rho$ is the density contrast, $\gamma_\kappa$, is the compressibility contrast, and superscript T denotes the transpose of the vector, $A(r_m)$ is a vector given by:

$$A^T(r_m) = [a_1(r_m)a_2(r_m) \ldots a_N(r_m)], B_n(r_m)$$

is a vector given by:

$$B_n^T(r_m) = [\cos(\theta_{m_1,n})a_1(r_m)a_n(r_m)\cos(\theta_{m_2,n})a_2(r_m)a_n(r_m) \ldots \cos(\theta_{m_N,n})a_N(r_m)a_n(r_m)],$$

$a_i$ is the integral of Green's function over the surface element i, i is 1 to N, and $\theta_{m_i,n}$ is the angle between a vector from the center of the transmitting element to a point where an inhomogeneity is located.

5. A method as recited in claim 4, wherein the pseudo-spectrum $\varphi(r)$ is calculated according to the equation:

$$\Phi(r) = \frac{1}{\sum_{\sigma_p=0} |u_p^\dagger A(r)|^2} + \frac{1}{\sum_{\sigma_p=0} \sum_{n=1}^{N} |u_p^\dagger B_n(r)|^2}$$

where superscript † denotes the transpose of the complex conjugate of a vector or a matrix, $94_p$, are singular values, and $\mu_p$ is a left singular vector.

6. A method as recited in claim 1, wherein the diffraction response of each transducer element is a function of finite size effects of the array of transducer elements.

7. A method as recited in claim 1, wherein the step of receiving backscatter signal comprises:

dividing an imaging plane of the target region into a plurality of sub-regions;

imaging each sub-region in the plurality of sub-regions separately; and combining each sub-region to form an entire image of the target region.

8. An ultrasound imaging system for imaging of a medium, the system comprising:

(a) a processor; and (b) programming executable on said processor for:

(i) exciting a first transducer element in an array of transducer elements to direct an ultrasound signal into a target region of the medium;

(ii) receiving a backscatter signal from the target region within the medium from the array of transducer elements;

(iii) generating an inter-element transfer matrix of the received backscatter signal;

(iv) said inter-element transfer matrix comprising density contrast data relating to one or more scatterers within said medium;

(v) generating a generalized time-reversal (TR) matrix from the inter-element transfer matrix; and (vi) generating a pseudo-spectrum for generalized TR-Music imaging of the target region, said pseudo-spectrum comprising density contrast data relating to one or more scatterers within said medium, wherein generating the inter-element transfer matrix comprises calculating the inter-element transfer matrix as a function of an electro-mechanical response of each transducer element in the array, a diffraction response of each transducer element in the array, and attenuation in the target region.

9. A system as recited in claim 8: wherein said inter-element transfer matrix further comprises compressibility contrast data; and wherein said pseudo-spectrum comprises density contrast data and compressibility contrast data relating to one or more scatterers within said medium.

10. A system as recited in claim 9, wherein the density contrast data and compressibility contrast data are obtained from least squares estimation of a pseudo-spectrum generated from TR-MUSIC imaging.

11. A system as recited in claim 9, wherein said inter-element transfer matrix K is calculated according to the function:

$$K = F(\omega)\sum_{m=1}^{M} \gamma_\kappa(r_m)A(r_m)A^T(r_m) + \gamma_\rho(r_m)[\begin{array}{cccc} B_1(r_m) & B_2(r_m) & \ldots & B_N(r_m) \end{array}]$$

where $F(\omega)$ is a electromechanical transfer function, M is the number of the scatterers within said medium, $r_m$ is a location of an $m^{th}$ point scatter, $\gamma_\rho$ is the density contrast, $\gamma_\kappa$ is the compressibility contrast, and superscript T denotes the transpose of the vector, where $A(r_m)$ is a vector given by:

$$A^T(r_m) = [a_1(r_m)a_2(r_m) \ldots a_N(r_m)],$$

and where $B_n(r_m)$ is a vector given by:

$$B_n^T(r_m) = [\cos(\theta_{m_1,n})a_1(r_m)a_n(r_m)\cos(\theta_{m_2,n})a_2(r_m)a_n(r_m) \ldots \cos(\theta_{m_N,n})a_N(r_m)a_n(r_m)],$$

$a_I$ is the integral of Green's function over the surface element i, i is 1 to N, and $\theta_{m_i,n}$ is the angle between a vector from the center of the transmitting element to a point where an inhomogeneity is located.

12. A system as recited in claim 11, wherein the pseudo-spectrum is calculated according to the equation:

$$\Phi(r) = \frac{1}{\sum_{\sigma_p=0} |u_p^\dagger A(r)|^2} + \frac{1}{\sum_{\sigma_p=0} \sum_{n=1}^{N} |u_p^\dagger B_n(r)|^2}$$

wherein superscript † denotes the transpose of the complex conjugate of a vector or a matrix, $\sigma_p$, are singular values, and $\mu_p$ is a left singular vector.

13. A system as recited in claim 8, wherein the diffraction response of each transducer element is a function of the finite size effects of the array of transducer elements.

14. A system as recited in claim 8, wherein the step of receiving the backscatter signal comprises:
   dividing an imaging plane of the target region into a plurality of sub-regions;
   imaging each sub-region in the plurality of sub-regions separately; and
   combining each sub-region to form an entire image of the target region.

\* \* \* \* \*

UNITED STATES PATENT AND TRADEMARK OFFICE
CERTIFICATE OF CORRECTION

PATENT NO. : 9,955,944 B2
APPLICATION NO. : 14/339791
DATED : May 1, 2018
INVENTOR(S) : Lianjie Huang et al.

It is certified that error appears in the above-identified patent and that said Letters Patent is hereby corrected as shown below:

In the Claims

Column 39, Line 45,         delete "$\gamma_\kappa,$"
Claim 4                     insert -- $\gamma_\kappa$ --

Column 40, Line 2,          delete "94 $_p,$"
Claim 5                     insert -- $\sigma_p,$ --

Column 41, Line 5,          delete "$a_I$"
Claim 11                    insert -- $a_i$ --

Signed and Sealed this
Twenty-second Day of October, 2019

Andrei Iancu
*Director of the United States Patent and Trademark Office*